United States Patent [19]

Witzel et al.

[11] Patent Number: 5,620,986
[45] Date of Patent: Apr. 15, 1997

[54] 17 UREA, THIOUREA, THIOCARBAMYL AND CARBAMYL4-AZASTEROID 5-REDUCTASE INHIBITORS USEFUL IN THE PREVENTION AND TREATMENT OF HYPERANDROGENIC DISORDERS

[75] Inventors: Bruce E. Witzel, Westfield; Richard L. Tolman, Warren, both of N.J.

[73] Assignee: Merck & Co., Inc., Rahway, N.J.

[21] Appl. No.: 338,574

[22] PCT Filed: May 17, 1993

[86] PCT No.: PCT/US93/04634

§ 371 Date: Mar. 1, 1995

§ 102(e) Date: Mar. 1, 1995

[87] PCT Pub. No.: WO93/23048

PCT Pub. Date: Nov. 25, 1993

Related U.S. Application Data

[63] Continuation-in-part of Ser. No. 886,645, May 20, 1992, abandoned.

[51] Int. Cl.$^6$ .......................... A61K 31/45; C07D 221/02
[52] U.S. Cl. .......................... 514/284; 514/253; 514/269;
544/238; 544/242; 544/243; 544/336; 544/337;
546/77
[58] Field of Search ................................ 514/284; 546/77

[56] References Cited

U.S. PATENT DOCUMENTS

| 2,227,876 | 1/1941 | Bolt ............................................. | 546/77 |
|---|---|---|---|
| 3,239,417 | 3/1966 | DiTullio et al. ........................... | 546/77 |
| 3,264,301 | 8/1966 | Doorenboos ................................ | 546/77 |
| 3,285,918 | 11/1966 | Doorenboos et al. ..................... | 546/77 |
| 4,220,775 | 9/1980 | Rasmusson et al. ...................... | 546/77 |
| 4,317,817 | 3/1982 | Blohm et al. . | |
| 4,377,584 | 3/1983 | Rasmusson et al. ...................... | 546/77 |
| 4,596,812 | 6/1986 | Chidsey, III et al. . | |
| 4,732,897 | 3/1988 | Cainelli et al. ............................ | 546/77 |
| 4,760,071 | 7/1988 | Rasmusson et al. ...................... | 546/77 |
| 4,845,104 | 7/1989 | Carlin et al. .............................. | 546/77 |
| 4,859,681 | 8/1989 | Rasmusson et al. ...................... | 546/77 |
| 4,882,319 | 11/1989 | Holt et al. ................................. | 514/79 |
| 4,910,226 | 3/1990 | Holt et al. ................................. | 514/319 |
| 5,049,562 | 9/1991 | Rasmusson et al. ...................... | 546/77 |
| 5,110,939 | 5/1992 | Holt et al. ................................. | 548/250 |
| 5,116,983 | 5/1992 | Bhattacharya et al. ................... | 546/77 |
| 5,494,914 | 2/1996 | Labrie et al. .............................. | 514/284 |

FOREIGN PATENT DOCUMENTS

| 970692 | 7/1975 | Canada . |
|---|---|---|
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375349 | 6/1990 | European Pat. Off. . |
| 0375347 | 6/1990 | European Pat. Off. . |
| 0375345 | 6/1990 | European Pat. Off. . |
| 0375344 | 8/1990 | European Pat. Off. . |
| 0572166A1 | 12/1993 | European Pat. Off. . |
| 1465544 | 11/1965 | France . |
| WO91/12261 | 8/1991 | WIPO . |
| WO93/23053 | 11/1993 | WIPO . |
| 9323048 | 11/1993 | WIPO . |

OTHER PUBLICATIONS

Brooks et al, Steroids, vol. 47, No. 1 (1986), "5 Alpha–reductase inhibitory . . . activities of some 4–aza–steroids in the rat", pp. 1–19.

Voight et al., Endocrinology, vol. 92 (1973), "The antiandrogenic action of 4–androsten–3–one–17beta–carboxylic acid and its methyl ester on hamster flank organ", pp. 1216–1222.

Geldof et al., Eur. J. Cancer, vol. 26, No. 2 (1990), "Enzyme inhibitors in hormone dependent prostate cancer growth", p. 188.

Kedderis et al., Toxicol. Appl. Pharmacol., vol. 93 (1988), "Studies with nitrogen–containing steroids and freshly isolated rat hepatocytes: Role of cytochrome p–450 in Detoxification", pp. 403–412.

(List continued on next page.)

Primary Examiner—Donald G. Daus
Attorney, Agent, or Firm—Catherine D. Fitch; Melvin Winokur; Joanne Giesser

[57] ABSTRACT

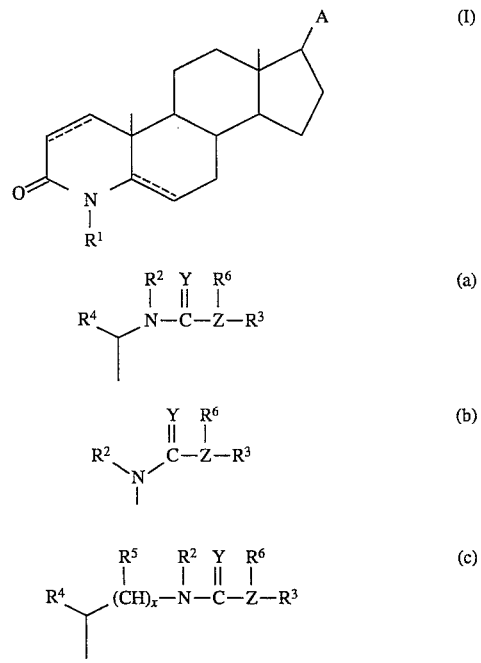

Novel substituted 4-azasteroid 5-α-reductase inhibitors of formula (I), wherein A is (a), (b) or (c), are claimed as well as pharmaceutically acceptable salts and formulations thereof. These compounds are effective inhibitors of testosterone 5α-reductase(s) and are thus useful in the treatment of a number of hyperandrogenic conditions including benign prostatic hypertrophy, acne, seborrhea, female hirsutism, and male and female pattern baldness (alopecia).

18 Claims, No Drawings

OTHER PUBLICATIONS

Geldof et al., J. Cancer Res. Clin. Oncol., vol. 118 (1992), "Consideration of the use of 17beta-N, N-diethylcarbamoyl-4-methyl-4-aza-5alpha-androstan-3-one (4MA), a 5 alpha-reductase inhibitor, in prostate cancer therapy", pp. 50–55.

The Daily (Tuesday, May 7, 1996), "New Data on Proscar, Abbott's Hytrin Show Conflicting Results".

Wall Street Journal (Tuesday, May 7, 1996), "Study Finds Abbott's Prostate Drug is Much More Effective than Merck's", p. B4.

Endo., vol. 91, No. 2, pp. 427–437 (1972) by Neri, et al., "A Biological Profile of a Non-steroidal Antiandrogen, SCH 13521 . . . ".

Steroids, 14, 269–283(1969), by Nayfeh, et al., "Metabolism of Progesterone by Rat Testicular Homogenates–III".

J. Pharm. Sci., 62, No. 4, pp. 638–640 (1973) by Doorenbos & Solomons, "Synthesis & Antimicrobial Properties of 17 Beta–Isopentyloxy–4–Aza–5 Alpha–Androstane and the 4–Methyl Derivative".

J. Pharm. Sci., 60, No. 8, pp. 1234–1235 (1971) by Doorenbos & Brown, "4.17 Alpha–Dimethyl–4–Aza–5 Alpha–Androstan–17 beta–ol Acetate & Related Azasteroids".

J. Pharm., 63, No. 4, pp. 620–622 (1974) by Doorenbos & Kim, "Synthesis & Evaluation of Antimicrobial Properties of Amidinoazaandrostanes and Guanidinoazaandrostanes".

J. Med. Chem. (1986) 29 (11): pp. 2298–3115 by Rasmusson, et al., "Aza Steroids: Structure–Activity Relationships . . . ".

The Prostate (1986) 9 (1): pp. 65–75 by Brooks, et al., "Prostatic Effects Induced in Dogs By . . . 5 alpha–Reductase Inhibitors".

Endocr. (1985) 117 (2): pp. 571–579, by Liang, et al., "Species Differences in Prostatic Steroidal 5 Alpha–Reductases of Rat, Dog and Human".

J. Med. Chem. (1984) 27 (12)¤ pp. 1690–1701, by Rasmusson, et al., "Azasteroids as Inhibitors of Rat Prostatic 5 alpha–reductase".

J. Org. Chem. (1981) vol. 46, No. 7, pp. 1442–1446, T. Back, et al., "N–Chloroazasteroids . . . ".

Chem. Abstracts, vol. 95, 109055j, by T. Liang, et al. "Inhibition of 5 Alpha–Receptor Binding . . . by a 4–Methyl–4–Aza–Steroid".

JNCI, vol. 74, No. 2, pp. 475–481 (Feb. 1985), by N. Kadohama, et al., "Retardation of Prostate Tumor Progression in the Noble Rat by 4–Methyl–4–Aza–Steroid Inhibitors of 5 Alpha–Reductase".

The Prostate, vol. 10, pp. 189–197 (1987) by G. Androile, et al., "The Effect of 4MA . . . on the Growth of . . . Human Tumors . . . ".

J. Endocr., vol. 57, pp. 111–121 (1973) by K. D. Bingham, et al., "The Metabolism of Testosterone by Human Male Scalp Skin".

Toxicol. Appl. Pharmacol., vol. 103, pp. 222–227 (1990) by G. L. Kedderis, et al., "Studies With Nitrogen Containing Steroids . . . ".

Bioinorganic Chemistry, 17, pp. 372–376 (1986) by B. W. Metcalf, et al., "Patent Inhibition of Human Steroid . . . by 3–Androstene–3–Carboxylic Acid".

Biochemistry, 1990, vol. 29, pp. 2815–2824, by M. A. Levy, et al., "Inhibition of Rat Liver Steroid 5 Alpha–Reductase . . . ".
ba
I. Med. Chem., 1990, vol. 33, pp. 943–950, by D. A. Holt, et al., "Steroidal A Ring Carboxylic Acids . . . ".

J. Steroid Biochem., vol. 34, Nos. 1–6, pp. 571–575 (1989), by M. A. Levy, et al., "Interaction Between Rat Prostatic 5 Alpha–Reductase . . . ".

J. Med. Chem., vol. 33, pp. 937–942 (1990) by D. A. Holt, et al., "Steroidal A Ring Aryl Carboxylic Acids".

TIPS, Dec. 1989, vol. 10, pp. 491–495, by D. W. Metcalf, et al., "Inhibitors of . . . 5 Alpha–Reductase in Benign Prostatic Hyperplasia . . . ".

Steroids, vol. 35, No. 3 (Mar. 1980) pp. 1–7, by L. Murphy, et al., "Effect of Estradiol on a . . . Binding Protein in the Uterus of the Mouse".

Prostate, vol. 9, pp. 311–318 (1986) by N. Stone, et al., "Estrogen Formation in Human Prostatic Tissue . . . ".

Steroids, vol. 47, No. 1, pp. 1–19 (1986) by J. R. Brooks, et al., "5 Alpha–Reductase Inhibitiory . . . Activities of Some 4–Azasteroids . . . ".

Lancet, No. 1986, No. 8515, pp. 1095–1096, by F. Labrie, et al. "Combination therapy in prostate cancer".

J. Clin. Endocrin. and Metab., vol. 55, No. 1, pp. 188–193 (1987), by R. Rittmaster, et al., "The Effects of . . . a 5 Alpha–Reductase Inhibitor . . . ".

J. Clin. Endocrin and Metab., vol. 74, No. 2, pp. 345–350 (1990), by A. Diani, et al., "Hair Growth Effects of Oral Administration of Finasteride . . . ".

J. Clin. Endocrinol. Metab. 67, No. 4, pp. 808–816 (1988), by N. Bruchovsky, et al., "Kinetic Parameters of 5 Alpha–Reductase Activity in Stroma & Epithelium of Normal Hyperplastic & Carcinomatous Human Prostates".

J. Steroid Biochem, 26, (3) pp. 349–353 (1987), by R. Hudson, "Comparison of Nuclear 5 Alpha–Reductase Activities in the Stromal and Epithelial Fractions of Human Prostatic Tissue".

J. Biol. Chem. 251, (19) pp. 5895–5900 (1976), by R. J. Moore, et al., "Steroid 5 Alpha–Reductase in Cultured Human Fibroblasts".

J. Biol. Chem. 264, (27) pp. 16249–16255 (1989), by S. Andersson, et al., "Expression Cloning & Regulation of steroid 5 alpha–Reductase, an Exzyme Essential for Male Sexual Differentiation".

Proc. Nat'l Acad. Science 87, pp. 3640–3644 (1990), by S. Andersson, et al., "Structural & Biochemical Properties of cloned and expressed human and rat steroid 5 alpha–reductases".

Nature 354, pp. 159–161 (Nov. 14, 1991), by S. Andersson, et al., "Deletion of Steroid 5 Alpha–Reductase–2 Gene in Male Pseudohermaphroditism".

Biol. of Reproduction, vol. 46, pp. 168–173 (1992), by J. D. Wilson, "Syndromes of Androgen Resistance".

J. Cancer Res. Clin. Oncol. 118, pp. 50–55 (1992), by A. Geldof, et al., "Consideration of the Use of . . . 4MA . . . in Prostate Cancer Therapy".

The Prostate 18, pp. 215–227 (1991), by J. Brooks, et al., "Effect of Castration, DES, Flutamide, and MK–906 on Growth of the Dunning Rat Prostatic Carcinoma . . . ".

Eur. J. Pharm. 183(5), p. 1757 (1990), by Y. Masubuchi, et al., "Lack of DHT Inhibition . . . by Treatment of 4MA . . . ".

Diani et al "Hair Growth Effects of Oral Administration of Finasteride, A Steroid 5 Alpha Reductase Inhibitor, Alone and in Combination witTopical Minoxidil in the Balding Stumptail Macaque", Jour. Clinical Endoc & Meta. 72:345–50 (1992).

Stinson, "Prostate Drug Proscar Cleared for Marketing", Chem. & Eng. News, Jun. 19, 1992 pp. 7–8.

Helliker, "Alopecia Sufferers Seek to Suffer Less, and Not in Silence", Wall St. Journal Jun. 7, 1991, pp. A1, A7.

Burger, "Medicinal Chemistry 2ed", Interscience, NY 1960, p. 42.

17 UREA, THIOUREA, THIOCARBAMYL AND CARBAMYL4-AZASTEROID 5-REDUCTASE INHIBITORS USEFUL IN THE PREVENTION AND TREATMENT OF HYPERANDROGENIC DISORDERS

CROSS REFERENCE TO RELATED APPLICATIONS

This application is a national phase application under 35 U.S.C. § 371 of International application PCT US93/04634 filed May 17, 1993, which is a continuation in part of application Ser. No. 886,645, filed May 20, 1992, now abandoned.

BACKGROUND OF THE INVENTION

The present invention is directed to novel urea, thiourea, thiocarbamyl and carbamyl 4-azasteroidal 5-alpha-reductase inhibitors.

The art reveals that certain undesirable physiological manifestations, such as acne vulgaris, seborrhea, female hirsutism, male pattern baldness and benign prostatic hypertrophy, art the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation. A number of 4-aza steroid compounds are known in the art that are 5α-reductase inhibitors. For example, see U.S. Pat. Nos. 2,227,876, 3,239,417, 3,264,301 and 3,285,918; French Patent No. 1,465,544; Doorenbos and Solomons, J. Pharm. Sci. 62, 4, pp. 638–640 (1973); Doorenbos and Brown, J..Pharm. Sci., 60, 8, pp. 1234–1235 (1971); and Doorenbos and Kim, J. Pharm. Sci. 63, 4, pp. 620–622 (1974).

In addition. U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. describe 4-aza-17β-substituted-5α-androstan-3-ones which are said to be useful in the treatment of DHT-related hyperandrogenic conditions.

However, despite the suggestion in the prior art that hyperandrogenic diseases are the result of a single 5α-reductase, there are reports regarding the presence of other 5α-reductase isozymes in both rats and humans. For example, in human prostate, Bruchovsky, et al. (See J. Clm. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. A sequence of this rat gene was later used to select a human prostatic cDNA encoding a 5α-reductase termed "5α-reductase 1". (See Proc. Nat'l. Acad. Sci. 87, p. 3640–3644, 1990.)

More recently, a second, more abundant reductase (5α-treductase 2) has been cloned from human prostate with properties identified with the form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme is associated with hair follicles.

Thus, the art supports the existence of at least two genes for 5α-reductase and two distinct isozymes of 5α-reductase in humans. Both forms are present in prostatic tissue in which, 5α-reductase 2, is the more abundant, and the other isozyme, 5α-reductase 1, is believed to be more abundant in scalp tissue.

In the treatment of hyperandrogenic disease conditions. e.g. benign prostatic hyperplasia (BPH) it would be desirable to have one drug entity which is active against both enzymes 1 and 2 in the prostate to substantially inhibit dihydrotesterone (DHT) production. Alternatively, it would be desirable to have a drug entity which is highly selective for inhibiting the scalp associated enzyme 5α-reductase 1, for use in treating diseases of the skin and scalp, e.g. acne and alopecia. This latter drug could be used in combination with PROSCAR® (finasteride) which is highly selective for the prostatic enzyme 5α-reductase 2 for combination therapy in the treatment of BPH.

SUMMARY OF THE INVENTION

The present invention is concerned with novel 4-azasteriodal ureas, thioureas, thiocarbamates and carbamates and pharmaceutical compositions and formulations thereof that are useful for inhibiting the 5α-reductase isozymes 1 and 2 and are particularly effective in selectively inhibiting the 5α-reductase 1 associated with the scalp and dually inhibiting both isozymes 1 and 2 in the oral, parental or topical treatment of benign prostatic hyperplasia, acne, female hirsutism, male pattern baldness, androgenic alopecia, prostatitis, and the treatment of prostatic carcinoma.

The present invention claims compounds of the formula:

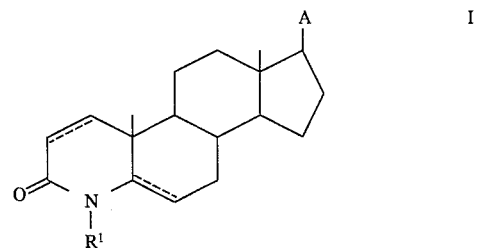

and the pharmaceutically acceptable salts thereof, wherein:

A is:

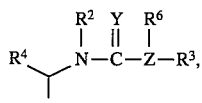 (a)

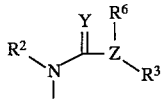 (b)

except when $R^2$ equals H, Y equals O, Z equals N and there is a 5αH, $R^6$ and $R^3$ cannot be independently selected from H, $C_{1-8}$ alkyl, $C_{3-6}$ cycloalkyl, phenyl or when $R^6$ and $R^3$ are taken together with the adjacent N to form a 5-6 membered ring comprising up to one other heteroatom selected from O or N, or

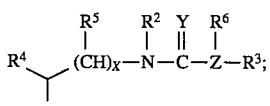 (c)

wherein
$R^1$ is:
  H, methyl or ethyl;
$R^2$ is:
  H, or
  $C_{1-20}$ alkyl:
$R^3$ is:
  H,
  amino,
  mono $C_1$-$C_4$alkylamino,
  di $C_1$-$C_4$alkylamino,
  mono $C_1$-$C_4$ alkylaminoaryl,
  di $C_1$-$C_4$ alkylammoaryl,
  $C_{1-20}$ alkyl,
  $C_{6-14}$ aryl,
  heteroaryl,
  $C_{6-14}$ aryl$C_{1-20}$alkyl,
  $C_{3-20}$cycloalkyl,
  $C_{3-20}$cycloalkyl$C_{1-20}$alkyl,
  heteroaryl$C_{1-20}$alkyl,
  $C_{2-20}$ alkenyl$C_{1-20}$alkyl,
  halo$C_{1-20}$alkyl,
  $C_{1-20}$alkyloxycarbonyl$C_{1-20}$alkyl,
  $C_{1-20}$alkyloxy$C_{1-20}$alkyl,
  carboxyl$C_{1-20}$alkyl,
  $C_{6-14}$ arylcarbonyl$C_{6-14}$aryl$C_{1-20}$alkyl,
  $C_{1-20}$alkylcarbonyl$C_{1-20}$alkyl,
  $C_{6-14}$ aryl$C_{1-20}$alkyloxycarbonyl$C_{1-20}$alkyl,
  heteroaryl$C_{1-20}$alkyloxycarbonyl$C_{1-20}$alkyl,
  hydroxyl$C_{1-20}$alkyl,
  halohydroxyl$C_{1-20}$alkyl,
  $C_{6-14}$ aryl$C_{1-20}$alkyloxy$C_{1-20}$alkyl,
  heteroaryl$C_{1-20}$alkyloxy$C_{1-20}$alkyl,
  carboxyl$C_{1-20}$alkyl,
  $C_{1-20}$alkylcarbonyl$C_{1-20}$alkyl.
  thiosulfato$C_{1-20}$alkyl,
  diaryl$C_{1-20}$alkyl of the formula:

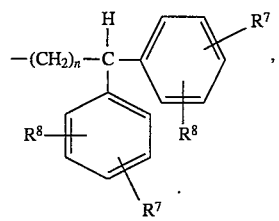

n equals 0-19;
triaryl$C_{1-20}$alkyl of the formula:

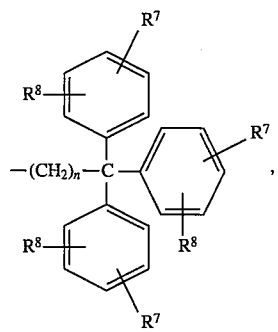

n equals 1-19;
  $C_{2-20}$ alkenyl,
  $C_{2-20}$ alkenyl$C_{1-20}$alkyl,
  $C_{2-20}$ alkyl$C_{1-20}$alkyl,
  $C_{6-14}$ aryl$C_{2-20}$alkynl$C_{1-20}$alkyl,
  heteroaryl$C_{2-20}$alkynyl$C_{1-20}$alkyl,
  $C_{1-20}$alkylthio$C_{1-20}$alkyl,
  $C_{1-20}$alkylsulfonyl$C_{1-20}$alkyl, or
  $C_{1-20}$alkylsulfonyl$C_{1-20}$alkyl;
$R^4$ is:
  H,
  $C_{1-20}$ alkyl,
  $C_6$aryl wherein aryl is a monocyclic system composed of 6-membered aromatic rings either unsubstituted or substituted with R wherein R is H, $C_{1-6}$ alkyl, aryl$C_{1-20}$alkyl with the alkyl groups unsubstituted or substituted with hydroxyl, $C_{1-8}$alkyloxy, carboxy $C_{0-10}$alkyl, or halogen or aryl directly substituted independently with amino, mono $C_1$-$C_4$ alkylamino, di $C_1$-$C_4$ alkylamino, mono $C_1$-$C_4$ alkylaminoaryl, di $C_1$-$C_4$ alkylaminoaryl, hydroxyl, halo$C_{1-20}$alkyl, carboxamido, benzoyl, $C_{1-20}$alkyloxy, $C_{1-20}$alkyl, $C_{2-20}$alkenyl, cyano, nitro, acetamide or halogen; or
  heteroaryl;
$R^5$ can be the same or different when x is greater than 1 and is:
  H, or
  $C_{1-12}$ alkyl,
  heteroaryl, or
  $C_{6-14}$ aryl;
$R^6$ is present when Z equals N and is independently
  H,
  $C_{1-20}$ alkyl, or
  equivalent to $R^3$; or taken together with $R^3$ and the N to which they are attached represent a heteroaryl ring system;

$R^7$ or $R^8$ are:

H,
$CH_3$,
$C_2H_5$,
carboxamido,
OH,
$OCH_3$,
$NO_2$,
CN,
F,
RS,
RSO,
$RSO_2$,
$R_2N$, where R can be the same or different selected from H, $C_1$-$C_4$ alkyl, or $C_6$-$C_{10}$ aryl;
Cl,
acetamido,
$OC_2H_5$,
$CF_3$,
isopropyl, or
isobutyl; n equals 1–10 and the $C_{1-20}$alkyl portion is optionally substituted with $R_5$;

Y is:
O, or
S;

Z is:
N, or
O;

x is an integer from 1–25 and dashes indicate a double bond is optionally present.

Advantageously, compounds of the following formula are disclosed in the present invention.

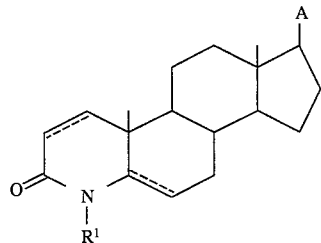

and the pharmaceutically acceptable salts thereof, wherein:
A is:

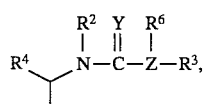

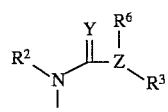

except when $R^2$ equals H, Y equals O, Z equals N and there is a 5αH, $R^6$ and $R^3$ cannot be independently selected from H, $C_{1-8}$ alkyl, $C_{3-6}$ cycloalkyl, phenyl or when $R^6$ and $R^3$ are taken together with the adjacent N to form a 5–6 membered ring comprising up to one other heteroatom selected from O or N, or

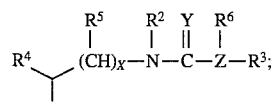

wherein
$R^1$ is:
H, methyl or ethyl;
$R^2$ is:
H, or
$C_{1-20}$ alkyl;
$R^3$ is:
H, $C_{1-20}$alkyl is a straight or branched chain alkane of up to 20 carbon atoms;

$C_{6-14}$ aryl wherein aryl is a mono or polycyclic system composed of 6-membered aromatic rings either unsubstituted or substituted with R wherein R is H, $C_{1-6}$ alkyl, aryl$C_{1-20}$alkyl with the alkyl groups unsubstituted or substituted with hydroxyl, $C_{1-8}$alkyloxy, carboxy $C_{0-10}$alkyl, or halogen or aryl directly substituted independently with amino, mono $C_1$-$C_4$ alkylamino, di $C_1$-$C_4$ alkylamino, mono $C_1$-$C_4$ alkylaminoaryl, di $C_1$-$C_4$ alkylaminoaryl, hydroxyl, halo$C_{1-20}$alkyl, carboxamido, benzoyl, $C_{1-20}$alkyloxy, $C_{1-20}$alkyl, $C_{2-20}$alkenyl, cyano, nitro, acetamido or halogen; heteroaryl which is a mono or polycyclic system composed of 5- or 6-membered aromatic rings consisting of 1, 2, 3 or 4 heteroatoms chosen from N, O, or S and either unsubstituted or substituted with R or independently with hydroxyl, $C_{1-20}$alkyloxy, $C_{1-20}$alkyl, benzoyl, carboamide, acetamide, halogens, $C_{2-20}$alkenyl, cyano, nitro, or haloalkyl directly bonded to the aromatic carbon atoms(s);

$C_{6-14}$ aryl$C_{1-20}$alkyl of the formula:

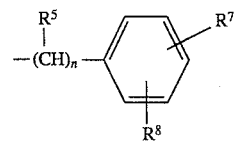

wherein the aromatic ring is optionally and independently substituted with $R^7$ and $R^8$ wherein $R^7$ and $R^8$ are H,
$CH_3$,
$C_2H_5$,
carboxamido,
OH,
$OCH_3$,
$NO_2$,
CN,
F,
RS,
RSO,
$RSO_2$,
$R_2N$, where R can be the same or different selected from H, $C_1$-$C_4$ alkyl, or $C_6$-$C_{10}$ aryl;
Cl,
acetamido,
$OC_2H_5$,
$CF_3$, isopropyl, or isobutyl; n equals 1–10 and the $C_{1-20}$alkyl portion is optionally substituted with $R^5$;

HeteroarylC$_{1-20}$alkyl of the formula:

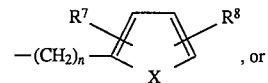
, or

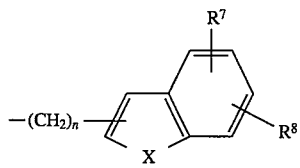

wherein X equals O, S, or NR; and n equals 1–20:

$C_{1-20}$alkylsulfonylC$_{1-20}$alkyl, $C_{1-20}$alkylthioC$_{1-20}$alkyl, $C_{1-20}$alkylsulfinylC$_{1-20}$alkyl of the formula:

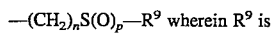

CH$_3$,
C$_2$H$_5$,
C$_3$H$_7$,
C$_4$H$_9$,
isopropyl,
isobutyl,
sec-butyl,
t-butyl,
isopentyl,
neopentyl, or
ixohexyl; n equals 1–15 and p=0–2;

$C_{1-20}$alkyloxycarbonylC$_{1-20}$alkyl of the formula:

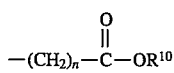

wherein $R^{10}$ is:
CH$_3$,
C$_2$H$_5$,
C$_3$H$_7$,
C$_4$H$_9$, or
C$_5$H$_{11}$; and n equals 1–20;

CarboxylC$_{1-20}$alkyl of the formula:

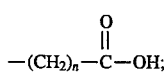

n=1–20;

$C_{1-20}$alkylcarbonylC$_{1-20}$alkyl of the formula

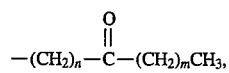

n equals 1–20;
m equals 0–19;

$C_{3-20}$cycloalkylC$_{1-20}$alkyl of the formula:

—(CH$_2$)$_n$—(cycloalkyl) wherein the cycloalkyl protion is a monocyclic, bicyclic, or polycyclic hydrocarbon of up to 20 carbon atoms wherein the rings are optionally substituted with $R^1$; and n=1–20;

ArylC$_{1-20}$alkyloxycarbonylC$_{1-20}$alkyl of the formula:

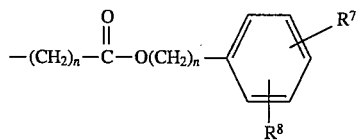

wherein $R^7$ and $R^8$ are as defined; n equals 1–20;

HeteroarylC$_{1-20}$alkyloxycarbonylC$_{1-20}$alkyl of the formula:

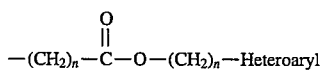

wherein Heteroaryl is as defined and n=1–20:

haloC$_{1-20}$ alkyl of the formula:

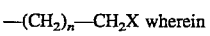

X equals Br, Cl, F or I; n is 1–19;

hydroxylC$_{1-20}$alkyl of the formula:

halohydroxylC$_{1-20}$alkyl of the formula:

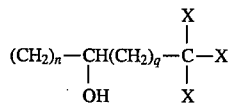

wherein n=1–18
q=0–18
n+q=0–18 and

X equals Br, Cl, F or I;

$C_{6-14}$ArylC$_{1-20}$alkyloxyC$_{1-20}$alkyl of the formula:

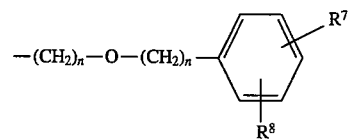

wherein $R^7$ and $R^8$ are as defined: n is 1–20;

ArylcarbonylarylC$_{1-20}$alkyl of the formula:

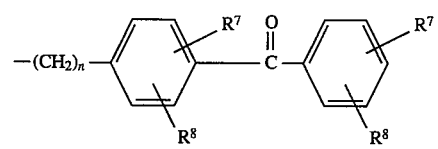

n equals 1–20;

DiarylC$_{1-20}$alkyl of the formula:

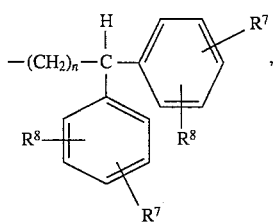

n equals 0–19;
TriarylC$_{1-20}$alkyl of the formula:

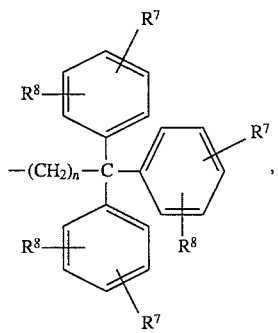

n equals 1–19;
Aryl C$_{2-20}$alkenyl of the formula:

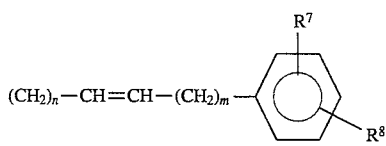

n=0–18
m=0–18
m+n=0–18;
R$^4$ is
H,
C$_{1-20}$alkyl,
C$_6$aryl wherein aryl is a monocyclic system composed of 6-membered aromatic rings either unsubstituted or substituted with R wherein R is H, C$_{1-6}$ alkyl, arylC$_{1-20}$alkyl with the alkyl groups unsubstituted or substituted with hydroxyl, C$_{1-8}$alkyloxy, carboxy C$_{0-10}$alkyl, or halogen or aryl directly substituted independently with amino, mono C$_1$-C$_4$ alkylamino, di C$_1$-C$_4$ alkylamino, mono C$_1$-C$_4$ alkylaminoaryl, di C$_1$-C$_4$ alkylaminoaryl, hydroxyl, haloC$_{1-20}$alkyl, carboxamido, benzoyl, C$_{1-20}$alkyloxy, C$_{1-20}$alkyl, C$_{2-20}$alkenyl, cyano, nitro, acetamide or halogen; or heteroaryl;
R$^5$ can be the same or different when x is greater than one and is;
H, or
C$_{1-12}$alkyl;
R$^6$ is present when Z equals N and is independently
H,
C$_{1-20}$ alkyl, or
equivalent to R$^3$; or taken together with R$^3$ and the N to which they are attached represent a heteroaryl ring system;

Y is:
O, or
S;
Z is:
N, or
O;
x is an integer from 1–10 and dashes indicate a double bond is optionally present.

The present invention is particularly concerned with providing a method of treating the hyperandrogenic conditions of androgenic alopecia, acne vulgaris, seborrhea, and female hirsutism by topical and/or oral administration, and a method of treating all of the above conditions as well as benign prostatic hyperplasia, prostatitis, the prevention and/or treatment of prostatic carcinoma, by oral or parenteral administration, of the novel compounds of the present invention.

The present invention is thus also concerned with providing suitable topical, oral and parenteral pharmaceutical formulations for use in the novel methods of treatment of the present invention.

DETAILED DESCRIPTION OF THE INVENTION

The present invention is concerned with novel 4-azasteroidal ureas, thioureas, and carbamates and pharmaceutical compositions and formulations thereof that are useful as testosterone 5α-reductase inhibitors to treat various hyperandrongenic conditions including acne vulgaris, seborrhea, female hitsutism, male and female pattern baldness, benign prostatic hypertrophy, prostatitis, androgenic alopecia, and the prevention and treatment of prostatic carcinoma. Advantageously, the compounds of the invention may be used to treat scalp disorders by selectively inhibiting 5α-reductase 1 or the compounds may be used as dual inhibitors of 5α-reductase 1 and 2 to treat the above disorders.

The present invention is concerned with compounds of the formula:

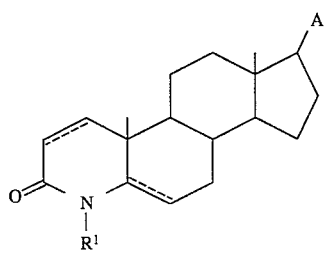

and the pharmaceutically acceptable salts thereof, wherein A is:

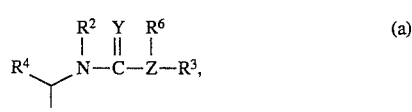

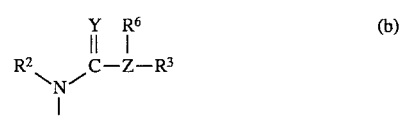

except when R$^2$ equals H, Y equals O, Z equals N, and there is a 5α H, R$^6$ and R$^3$ may not be independently selected from H, C$_{1-8}$ alkyl, C$_{3-6}$ cycloalkyl, phenyl or when R$^6$ and R$^3$ are taken together with the adjacent N to form a 5–6 membered ring comprising up to one other heteroatom selected from O or N, or

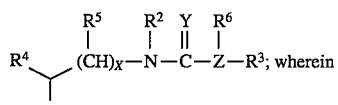; wherein $R^1$ is:
H,
$C_{1-20}$alkyl;
$R^2$ is:
H, or methyl or ethyl;
$R^3$ is:
H,
$C_{1-20}$ alkyl,
$C_{5-14}$ aryl,
heteroaryl,
$C_{5-14}$ aryl$C_{1-20}$alkyl,
heteroaryl$C_{1-20}$alkyl,
$C_{3-20}$ cycloalkyl,
$C_{3-20}$ cycloalkyl$C_{1-20}$alkyl,
$C_{2-20}$ alkenyl$C_{1-20}$alkyl,
halo$C_{1-20}$alkyl,
$C_{1-20}$ alkyloxy$C_{1-20}$alkyl,
$C_{1-20}$alkyloxycarbonyl$C_{1-20}$alkyl,
$C_{1-20}$ alkylthio$C_{1-20}$alkyl,
$C_{1-20}$ alkylsulfonyl$C_{1-20}$alkyl,
$C_{1-20}$alkylsulfinyl$C_{1-20}$alkyl,
carboxy$C_{1-20}$ alkyl,
$C_{6-14}$ arylcarbonylaryl$C_{1-20}$alkyl
$C_{1-20}$ alkylcarbonyl$C_{1-20}$alkyl,
$C_{6-14}$ aryl$C_{1-20}$ alkyloxycarbonyl$C_{1-20}$alkyl,
heteroaryl$C_{1-20}$alkyloxycarbonyl$C_{1-20}$alkyl,
halo$C_{1-20}$alkyl,
hydroxy$C_{1-20}$alkyl,
halohydroxyl$C_{1-20}$alkyl,
$C_{6-14}$ aryl$C_{1-20}$alkyloxy$C_{1-20}$alkyl,
heteroaryl$C_{1-20}$alkyloxy$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
$C_{6-14}$ aryl$C_{2-20}$alkynyl$C_{1-20}$alkyl, or
heteroaryl$C_{2-20}$alkynyl$C_{1-20}$alkyl;
$R^4$ is:
H,
$C_{1-20}$ alkyl,
heteroaryl, or
$C_{6-14}$ aryl;
$R^5$ can be the same or different when x is greater than 1 and is:
H,
$C_{1-20}$ alkyl,
heteroaryl, or
$C_{6-14}$ aryl;
$R^6$ is present when Z equals N and is
H, or
$C_{1-20}$ alkyl; or taken together with $R^3$ and the N to which they are attached represent a heteroaryl ring system;
Y is:
O, or
S;
Z is:
N, or
O;
x is an integer from 1–25, and dashes indicate a double bond is optionally present.

Compounds of the formula:

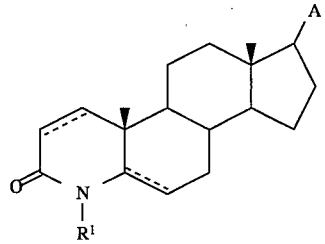

are representative of the compounds claimed in the instant invention. In a preferred embodiment. $R^1$ may be H or $CH_3$ and A may be as indicated as in Table 1. Particular representative chemical names are also listed in Table 1 adjacent to the respective side chain and specifically reflect whether the 1-position is saturated or unsaturated. Advantageously, $R^1$ is $CH_3$, A is as indicated in Table 1 and the 1 position is saturated. Unless otherwise indicated, the 17-position substituent is assumed to be on the beta configuration.

TABLE 1

| | Side Chain A | Compounds |
|---|---|---|
| (1) | ![N-C(=O)-N-CH3 side chain] | 4-Methyl-20-(N'-methyl-ureido)-5α-4-azapregn-1-en-3-one |
| | | 4-Methyl-20-(N'-methyl-ureido)-5α-4-azapregnan-3-one |

TABLE 1-continued

| | Side Chain A | Compounds |
|---|---|---|
| (2) | H O H<br>N—C—N—+ (t-butyl) | 17-(N'-t-butylureido-methyl)-4-methyl-5α-4-azaandrost-1-en-3-one |
| | | 17-(N'-t-butylureido-methyl)-4-methyl-5α-4-azaandrostan-3-one |
| (3) | H O H<br>N—C—N—Ph | 4-Methyl-17-(N'-phenyl-ureidomethyl)-5α-4-aza-androst-1-en-3-one |
| | | 4-Methyl-17-(N'-phenyl-ureidomethyl)-5α-4-aza-androstan-3-one |
| (4) | H O H<br>N—C—N—CH$_2$—CH$_2$—CH$_3$ | 4-Methyl-17-(N'-n-propyl-ureidomethyl)-5α-4-aza androst-1-en-3-one |
| | | 4-Methyl-17-(N'-n-propyl-ureidomethyl)-5α-4-aza-androstan-3-one |
| (5) | H O H<br>N—C—N(CH$_2$)$_7$CH$_3$ | 4-Methyl-17-(N'-n-octyl-ureidomethyl)-5α-4-aza-androstan-3-one |
| | | 4-Methyl-17-(N'-n-octyl-ureidomethyl)-5α-4-aza-androstan-3-one |
| (6) | O H<br>C—N—CH$_3$<br>HN | 4-Methyl-17-(N'-methyl-ureido)-5α-4-azaandrost-1-3n-3-one |
| | | 4-Methyl-17-(N'-methyl-ureido)-5α-4-azaandrost-1-an-one |
| (7) | O H<br>C—N—Ph<br>HN | 4-Methyl-17-(N'-phenyl-ureido)-5α-4-azaandrost-1-en-3-one |
| | | 4-Methyl-17-(N'-phenyl-ureido)-5α-4-azaandrost-an-3-one |
| (8) | O H<br>C—N—+ (t-butyl)<br>HN | 17-(N'-t-butylureido)4-methyl-5α-4-azaandrost-1-en-3-one |
| | | 17-(N'-t-butylureido)4-methyl-5α-4-azaandrostan-en-3-one |
| (9) | H O H<br>N—C—N—iPr | 17-(N'-isopropylureido-methyl)4-methyl-5α-4-azaandrost-1-en-3-one |

TABLE 1-continued

| Side Chain A | Compounds |
|---|---|
| | 17-(N'-isopropylureido-methyl)4-methyl-5α-4-azaandrostan-3-one |
| (10) $\underset{\|}{N}-\overset{O}{\underset{\|}{C}}-\overset{H}{N}-CH_2-CH_2-CH_3$ (with H above each N) | 4-Methyl-17β(N'-n-propyl-ureidomethyl)5α-4-aza-androstan-3-one |
| | 4-Methyl-17β(N'-n-propyl-ureidomethyl)5α-4-azaan-drost-1-en-3-one |
| (11) $\underset{\|}{N}-\overset{O}{\underset{\|}{C}}-\overset{H}{N}(CH_2)_7CH_3$ | 4-Methyl-17β-(N'-n-octyl-ureidomethyl)5α-4-azaan-drost-1-en-3-one |
| | 4-Methyl-17β-(N'-n-octyl-ureidomethyl)5α-4-azaan-drostan-3-one |
| (12) $\underset{\|}{\overset{H}{N}}-\overset{O}{\underset{\|}{C}}-\overset{H}{N}-Ph$ | 4-Methyl-17β-(N'-phenyl-ureido)-5α-4-azaandrost-an-3-one |
| | 4-Methyl-17β-(N'-phenyl-ureido)-5α-4-azaandrost-1-en-3-one |
| (13) $\underset{\|}{N}-\overset{O}{\underset{\|}{C}}-\overset{H}{N}-CH(CH_3)_2$ | 17β-(N'-Isopropylureido-methyl)-4-methyl-5α-4-azaandrostan-3-one |
| | 17β-(N'-Isopropylureido-methyl)-4-methyl-5α-4-azaandrostan-3-one |
| (14) iBu-NH-C(O)-N(iminodibenzyl) | 20-((Iminodibenz-5-yl)-carbonylaminomethyl)-4-methyl-5α-4-aza-pregan-3-one |
| | 20-((Iminodibenz-5-yl)-carbonylaminomethyl)-4-methyl-5α-4-aza-pregan-1-en-3-one |
| (15) -N(H)-C(O)-N(iminodibenzyl) | 17β-((Iminodibenz-5-yl)-carbonylaminomethyl)-4-methyl-5α-4-aza-andro-stan-3-one |
| | 17β-((Iminodibenz-5-yl)- |

| Side Chain A | Compounds |
|---|---|
| (16) ![structure] O=C(OCH2-CH(CH3)CH3)N(H)- | 17β-(Isobutyloxycarbonyl-aminomethyl)-4-methyl-5α-4-azaandrostan-3-one |
| | 17β-(Isobutyloxycarbonyl-aminomethyl)-4-methyl-5α-4-azaandrost-1-en-3-one |

(previous compound row continued: carbonylaminomethyl)-4-methyl-5α-4-aza-androstan-3-one)

The following additional compounds may also be prepared according to the procedures described in the instant specification.

20-(Ethoxycarbonylamino)-4-methyl-5-α-4-azapregnan-3-one,
20-(Benzyloxycarbonylaminomethyl)-5-α-4-azapregnan-3-one,
4-Methyl-17β-(N'-octadecylureidomethyl)-5-α-4-azaandrostan-3-one,
17β-(N'-Benzylureidomethyl)-5-α-4-azaandrostan-3-one,
4-Methyl-17β-(N'-methylureido)-5-α-4-azaandrostan-3-one,
4-Methyl-17β-(Isobutyloxycarbonylamino)-5-α-4-azaandrostan-3-one,
17β-(N'-(2-Ethylphenyl)ureidomethyl)-5-α-4-azaandrostan-3-one,
17β-(N'-Allylureido)-4-methyl-5-α-4-azaandrostan-3-one,
20-(N'-(3-Chlorophenyl)ureido)-5-α-4-azapregnan-3-one,
4-Methyl-20-(N'-phenylureido)-5-α-4-azapregnan-3-one,
20-(N'-p-Tolylureidomethyl)-5-α-4-azapregnan-3-one,
17β-(N'-(2,3-Dichlorophenyl)ureidomethyl)-4-methyl-5-α-4-azaandrostan-3-one,
17β-(N'-(4-Fluorophenyl)ureido)-5-α-4-azaandrostan-3-one,
20-(N'-(2-Ethoxyphenyl)ureidomethyl)-4-methyl-5-α-4-aza-pregnan-3-one,
17β-(N'-(3-Methoxyphenylureido)-5-α-4-azaandrostan-3-one,
4-Methyl-17β-(N'-(naphth-2-yl)ureidomethyl)-5-α-4-azaandrostan-3-one,
4-Methyl-17β-(N'-thiazol-2-ylureidomethyl)-5-α-4-azaandrostan-3-one,
4-Methyl-20-(N'-thien-2-ylmethylureido)-5-α-4-aza-pregnan-3-one,
17-(N'-(Adamant-1-yl)-thiouriedomethyl)-4-methyl-5-α-4-azaandrostan-3-one,
4-Methyl-17-N-(N'-4-(trifluoromethoxy)phenyl))-5-α-4-azaandrostan-3-one, and
17-((1-Adamantyloxy)-carbonylaminomethyl)-5-α-4-methyl-4-azaandrostan-3-one and the corresponding 1-en derivatives.

Synthesis of Testosterone 5α Reductase Inhibitors

Scheme 1 illustrates the synthesis of the intermediate oximes and amines used to produce compounds claimed in the instant invention.

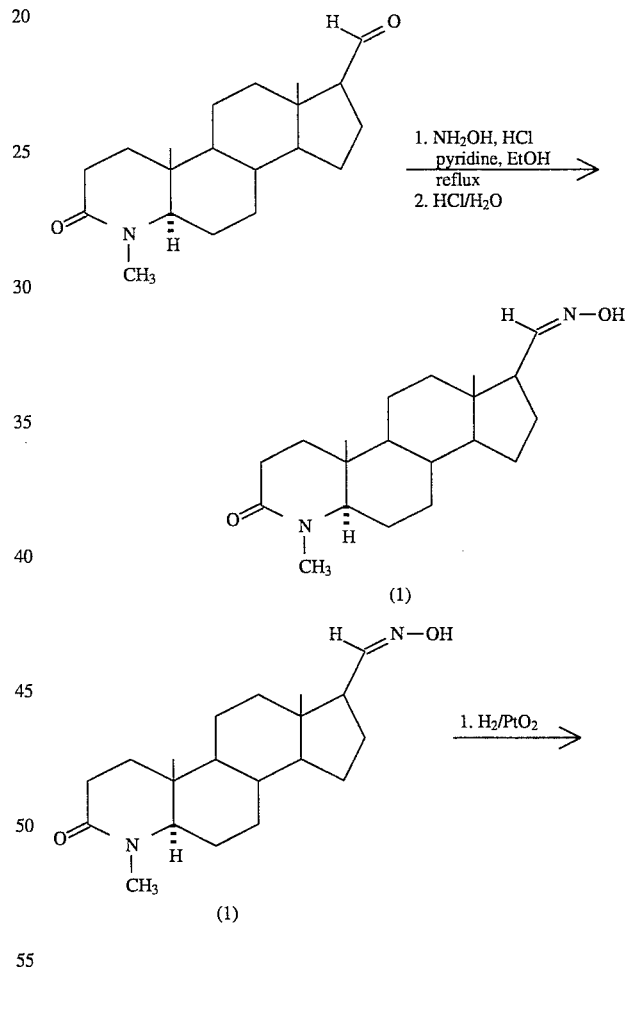

SCHEME 1

1. NH2OH, HCl
   pyridine, EtOH
   reflux
2. HCl/H2O (1)

1. H2/PtO2

(1)

-continued
SCHEME 1

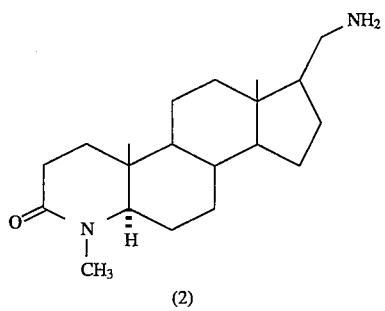
(2)

A stirred mixture of 4-methyl-3-oxo-5α-4-azaandrostan-17 carboxaldehyde, hydroxylamine hydrochloride, anhydrous pyridine, and anhydrous ethanol is refluxed gently under a nitrogen atmosphere for six to seven hours. After cooling, the ice-cooled mixture is diluted, with stirring, with a slight excess of chilled dilute hydrochloric acid. The suspension is then aged for about twenty minutes, filtered, washed with water and dried to give compound 1.

A mixture of the oxime (1), ethanol, glacial acetic acid and water is reduced in the presence of platinum oxide (PtO₂) until chromatographic analysis (TLC) indicates complete reduction to the amine (2). The filtered reaction n-fixture is concentrated in vacuo; the resultant residue is dissolved in chloroform (CHCl₃) and washed with fresh dilute sodium hydrogen carbonate solution. The chloroform phase is then dried with sodium sulfate (Na₂SO₄). Concentration of the resultant CHCl₃ solution followed by trituration of the residue with hexane/ether will yield 2 as a white solid.

The following amines (3–9) may readily be prepared according to the above process to yield the indicated compounds:

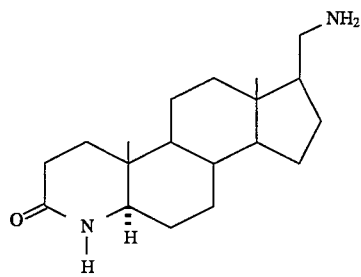
17-Aminomethyl-5-α-2-4-azaandrostan-3-one;

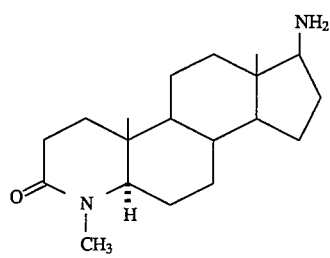
17-Amino-4-methyl-5-α-2-4-azaandrostan-3-one;

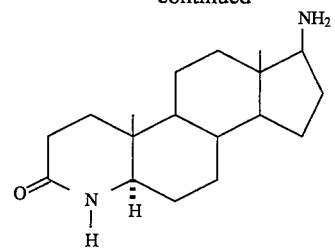
17-Amino-5-α-2-4-azaandrostan-3-one;

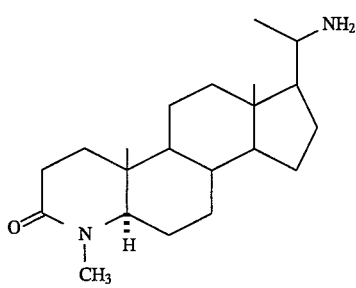
20-Amino-4-methyl-5-α-4-azapregnan-3-one;

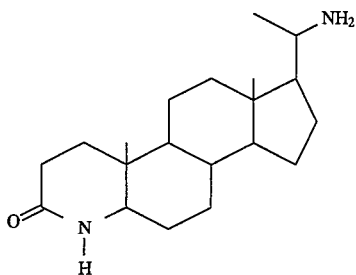
20-Amino-5-α-4-azapregnan-3-one;

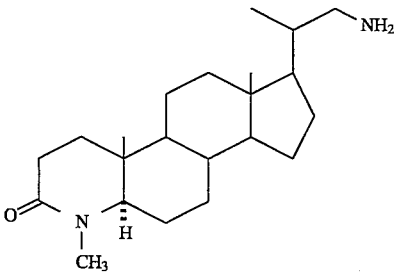
20-(Aminomethyl)-4-methyl-5-α-4-azapregnan-3-one;

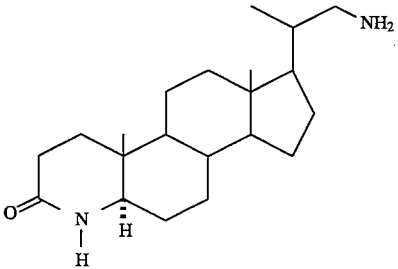
20-(Aminomethyl)-5-α-4-azapregnan-3-one;

As Scheme 1 indicates, the oximes useful as intermediates may readily be prepared by reacting a 4-azasteroidal aldehyde or ketone with hydroxylamine hydrochloride to form the corresponding oxime. The resultant oximes are subsequently reduced with hydrogen (H₂) and platinum oxide (PtO$_2$) or other suitable reducing agent to yield the respective amine. Product ureas or thioureas may be further alkylated with, for example, alkyl halides to give the corresponding R$^2$ alkylated compounds.

Scheme 2 illustrates the synthesis of the compound 17-(N'-t-butylureidomethyl)-4-methyl-5α-4-azaandrostan-3-one and is representative of a basic synthesis of compounds claimed in the instant invention in which an amine is reacted with a substituted isocyanate.

SCHEME 2

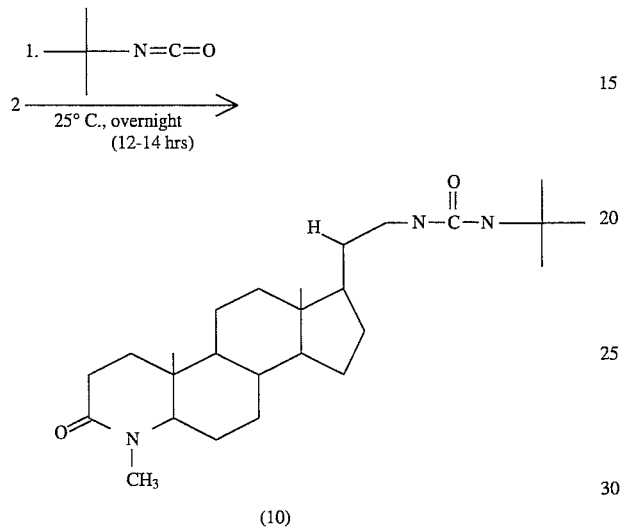

(10)

To a stirred solution of compound 2 in dry benzene at room temperature (25° C.) is added t-butylisocyanate or a suitable isocyanate. After stirring for 12–14 hours, the benzene is removed and the residue purified by flash chromatography (silica gel, EtOAc) to give 10 as a white solid. As Scheme 2 illustrates. 4-azasteroidal primary or secondary amines described in the instant invention are reacted with the desired substituted isocyanate, such as t-butyl isocyanate, to yield the target ureido derivative.

Representative substituted isocyanates include:
R$^3$—N=C=O
wherein R$^3$ equals
  H,
  C$_{1-20}$ alkyl,
  aryl,
  heteroaryl,
  arylC$_{1-20}$alkyl,
  C$_{3-20}$ cycloalkyl,
  C$_{3-20}$ cycloalkylC$_{1-20}$alkyl,
  heteroarylC$_{1-20}$alkyl,
  C$_{2-20}$ alkenylC$_{1-20}$alkyl,
  haloC$_{1-20}$alkyl,
  C$_{1-20}$ alkyloxyC$_{1-20}$alkyl,
  C$_{1-20}$ alkylcarbonylC$_{1-20}$alkyl,
  C$_{1-20}$alkyloxycarbonylC$_{1-20}$alkyl,
  arylC$_{1-20}$alkyloxycarbonylC$_{1-20}$alkyl,
  heteroarylC$_{1-20}$alkyloxycarbonylC$_{1-20}$alkyl,
  hydroxyC$_{1-20}$alkyl,
  arylC$_{1-20}$alkyloxyC$_{1-20}$alkyl,
  heteroarylC$_{1-20}$alkyloxyC$_{1-20}$alkyl,
  arylcarbonylarylC$_{1-20}$alkyl,
  diarylC$_{1-20}$alkyl,
  triarylC$_{1-20}$alkyl,
  C$_{2-20}$ alkenyl,
  C$_{2-20}$ alkenylC$_{1-20}$alkyl,
  C$_{2-20}$ alkynylC$_{1-20}$alkyl,
  arylC$_{2-20}$alkynylC$_{1-20}$alkyl,
  heteroarylC$_{2-20}$alkynylC$_{1-20}$alkyl,
  C$_{1-20}$ alkylthioC$_{1-20}$alkyl,
  C$_{1-20}$ alkylsulfonylC$_{1-20}$alkyl, or
  C$_{1-20}$ alkylsulfinylC$_{1-20}$alkyl, R$^3$ is also selected from
    -t-butyl,
  3-thienyl, -2-thienyl, -11-(isopropylthio)undecyl,
  -7-(carbomethoxy)heptyl, -(4-isobutylbenzene)ethyl,
  -7-(carboxy)heptyl, -acetylmethyl, -1-adamantylmethyl,
  -2-thienylmethyl, -2-(carbobenzyloxy)ethyl,
  -3,4 dimethoxyphenylmethyl,-phenyl, -5-bromopentyl,
  -11-hydroxyundecyl, -1(4-nitrophenyl)ethyl,
  -isopropylthiomethyl, -benzyloxymethyl,
  carbomethoxymethyl, -diphenylmethyl, -triphenylmethyl,
  -2-furyl, 4-isopropylphenyl, cyclohexylmethyl,
  4-methylcyclohexyl, 3-(3-Indolyl)propyl,
  3-Indoylmethyl, 4-isobutylbenzyl, 4-nitrobenzyl,
  3-acetamidomethyl, 4-ethoxybenzyl, hexadecyl,
  stearyl, 3,5 Bis(trifluoromethyl), 3-cyanobenzyl,
  heptaflouropropyl, 4-benoylbenzyl, 5-benztriaoolyl,
  3,5 diflourobenzyl, Bis (4-isopropylphenyl)methyl,
  2 hydroxybenzyl, methyl, allyl, n-propyl, n-octyl, isopropyl,
  isobutyl, ethyl, benzyl, octadecyl, 2(ethyl)phenyl,
  3(chloro)phenyl, 4(methyl)phenyl, 2,3(dichloro)phenyl,
  4(flouro)phenyl, 3(methoxy)phenyl, 2(ethoxy)phenyl,
  2(napthyl), or 2-thiazoyl or as specifically shown in the examples.

The primary or secondary amines disclosed in the instant invention may also be reacted with thioisocyanates of the formula

R$^3$—N=C=S to yield compounds claimed in the instant invention. In addition, as Scheme 3 shows, the described primary or secondary amines disclosed in the invention (such as 2) may be reacted with activated esters or thioesters, e.g. chloro formates, to yield compounds claimed in the instant invention. R$^3$ is defined as above.

Substituted isocyanates or thioisocyanates may readily be prepared by known synthetic methods. For example, phosgene or thiophosgene may be reacted with a suitable primary amine to give a chloroformamide or chlorosulfamide which loses HCl to form the respective substituted isocyanate or thioisocyanate. For reviews of isocyanate and thioisocyanate preparation, see Patai, "The Chemistry of Cyanates and their thio Derivatives." pt 2, Wiley, New York, pp 619–818 and 1003–1221 (1977). In addition, many isocyanates, thioisocyanates, esters or thioesters used to prepare the claimed compounds are commercially available or readily prepared from commercially available compounds.

SCHEME 3

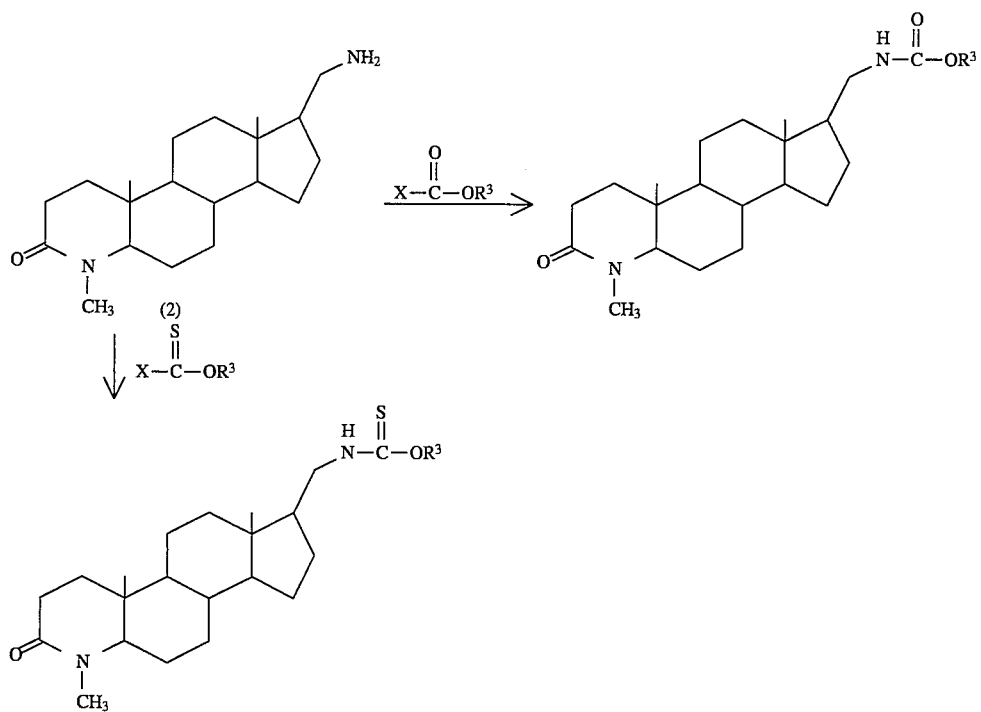

Ureas, thioureas, carbamates, and thiocarbamates claimed in the present invention may readily be obtained by following the basic procedure(s) described in Schemes 2 and 3. To further illustrate, compound 2 may be replaced by the amine (4) and reacted with t-butylisocyanate to yield 17-(N'-t-butylureido)-4-methyl-5α-4-azaandrostan-3-one (11) (Scheme 4).

SCHEME 4

(4) t-Butyl isocyanate →

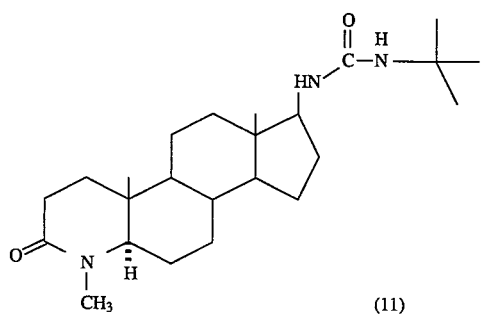

(11)

If compound 6 is reacted with methyl isocyanate under the conditions described for Scheme 2, 4-methyl-20-(N'-methylureido)-5α-4-azapregnan-3-one is obtained (12) (Scheme 5)

SCHEME 5

(6) + methyl isocyanate →

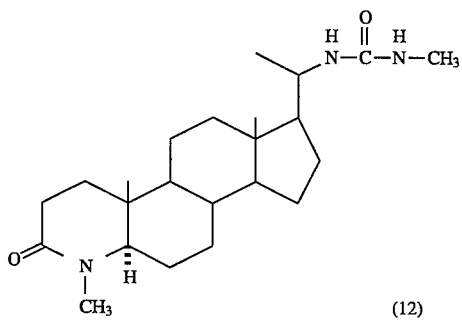

(12)

If compound 2 is reacted with phenyl isocyanate under the conditions described in Scheme 2, 4-methyl-17-(N'-phenyluriedomethyl)-5α-4-azaandro-stan-3-one is made (13) (Scheme 6).

SCHEME 6

2 + phenyl isocyanate →

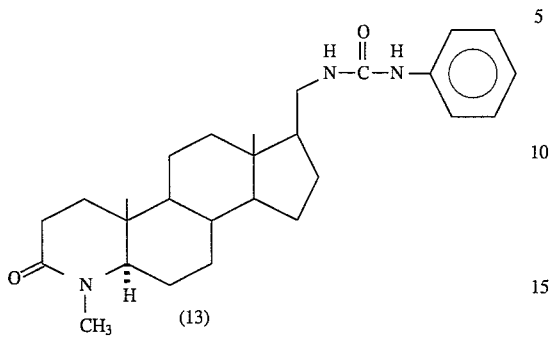

In addition, dehydrogenation of the 1,2 position may readily be accomplished by known synthetic methodology to produce the claimed 1-en derivatives. See U.S. Pat. No. 5,061,802 and Dolling et al., J. Am. Chem. Soc., 110, 3318–19 (1988).

Schemes 7, 8 and 9 further illustrate how compounds claimed in the instant invention may be prepared. In Scheme 7, the starting 4-azasteroid aldehyde or ketone (XIV), obtained by known synthetic methods, is reacted to form the oxime XV; reduced to the amine XVI and reacted with a substituted isocyanate, substituted thioisocyanate, activated ester or thioester to form XVII.

the amine XX and reacted with a substituted isocyanate, substituted thioisocyanate, activated ester or thioester to form XXI.

SCHEME 7

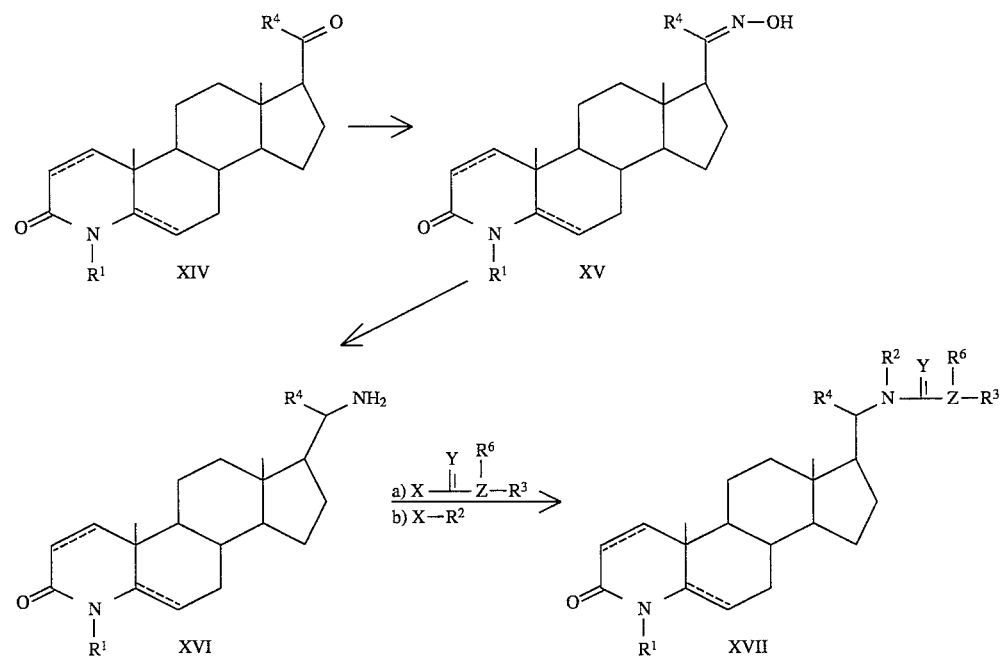

In Scheme 8, the identical procedure is followed using a generic 4-azasteroid (XVIII), prepared by known synthetic methods, to produce the oxime (XIX) which is reduced to

SCHEME 8
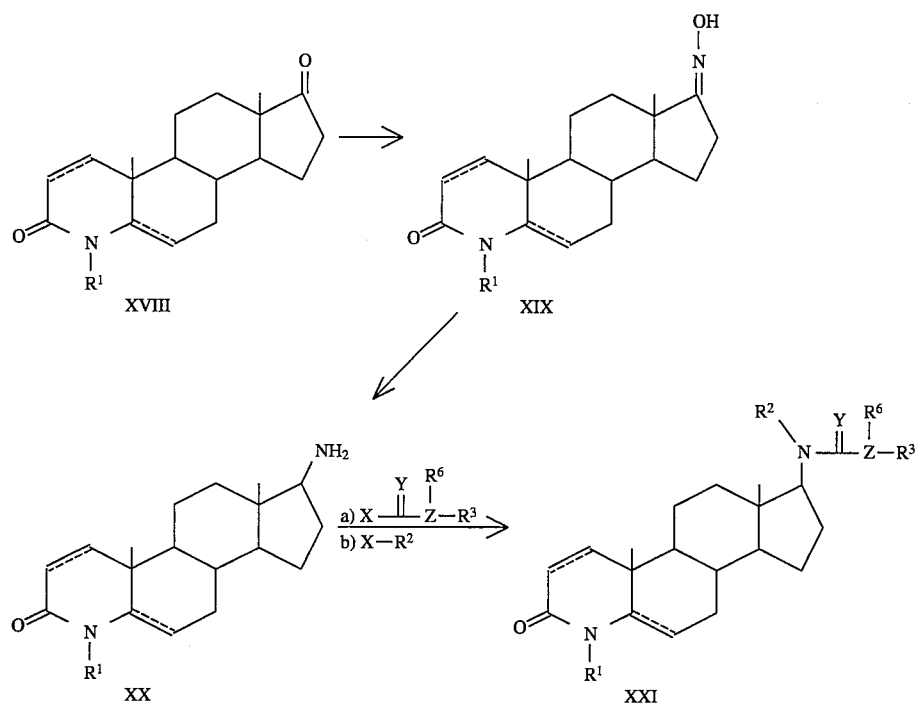
In Scheme 9, the generic 4-azasteroid XXII, also obtained from well known synthetic methodology, is reacted to form the oxime XXIII, which is further reduced to the amine XXIV, and reacted with a substituted isocyanate, substituted thioisocyanate, activated ester or thioester to form XXV.
SCHEME 9
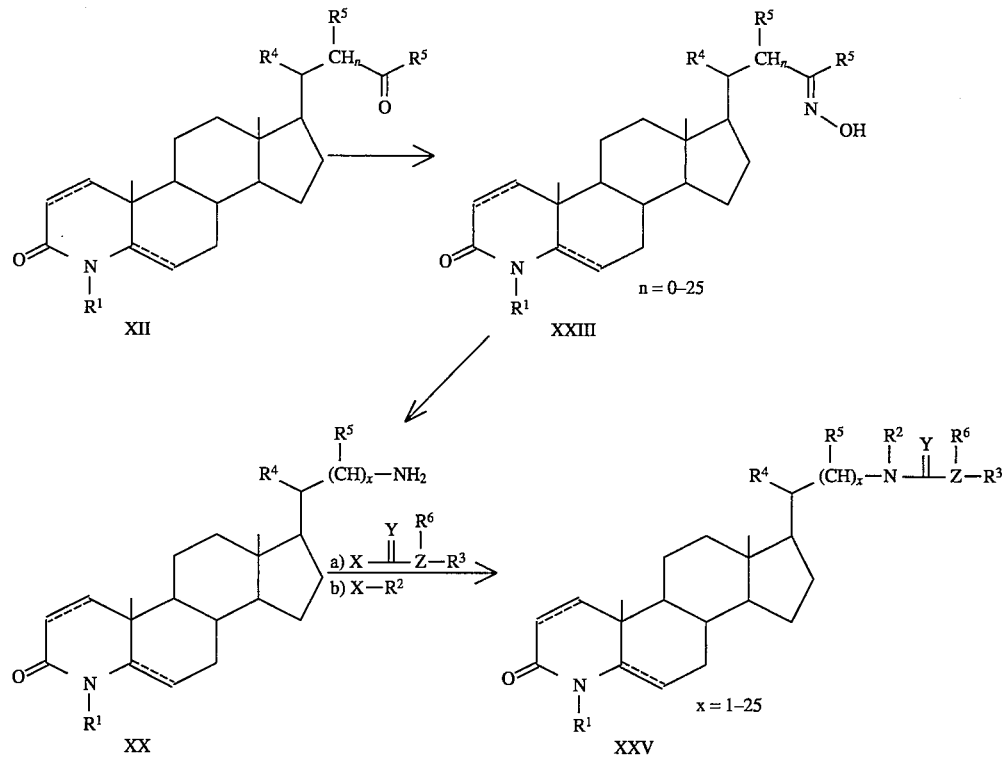

The starting 4-azasteroidal ketones used in the present invention may be prepared according to the basic procedures described in Scheme 10 via well known synthetic methodology.

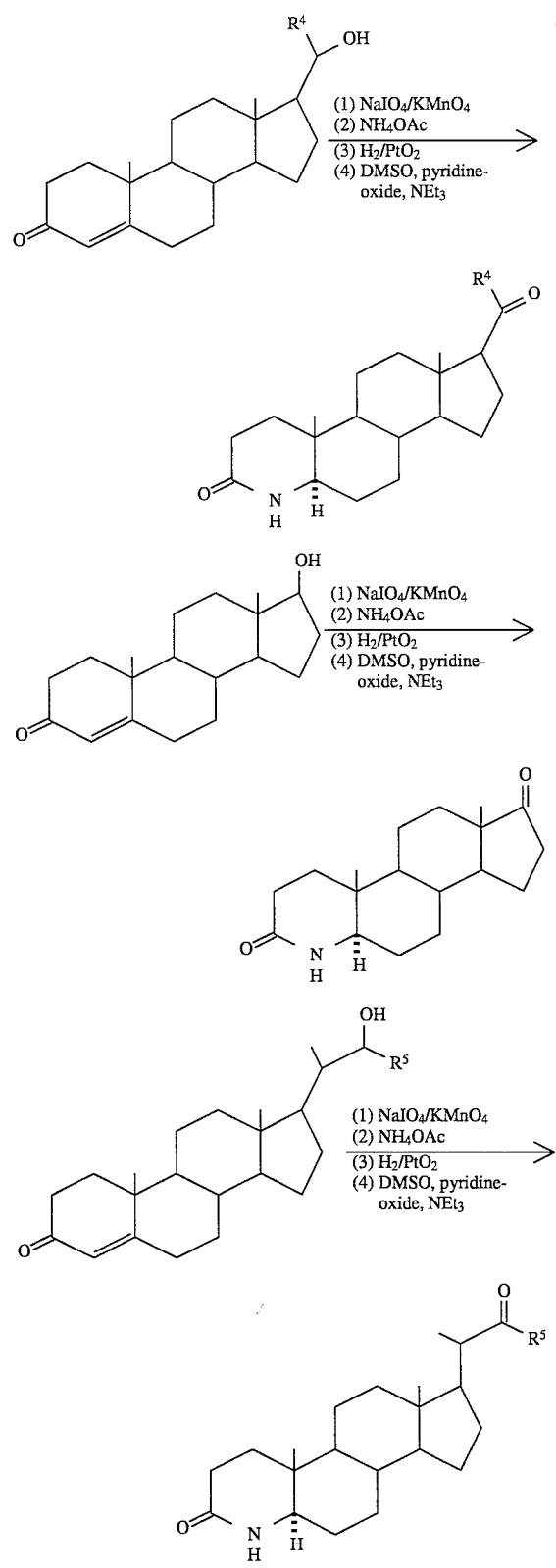

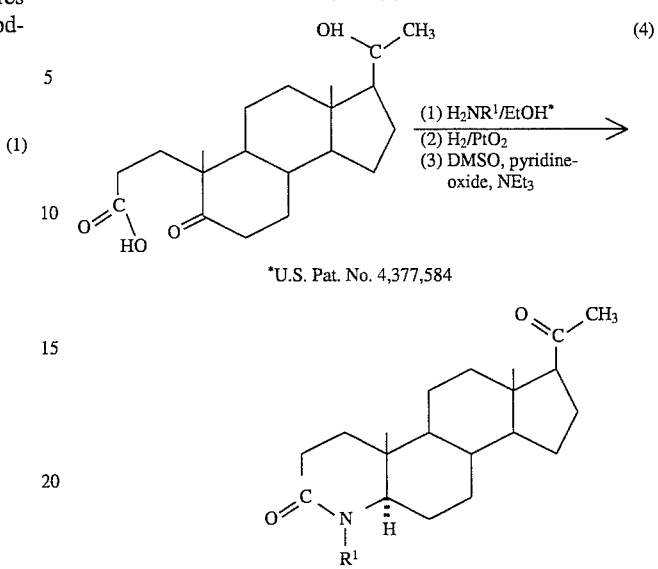

*U.S. Pat. No. 4,377,584

The following examples further describe the synthesis of compounds claimed in the instant invention.

Synthesis of Starting 4-Azasteroid Oximes

EXAMPLE 1

1) 4-Methyl-3-oxo-5α-4-azaandrostan-17-carboxaldehyde Oxime

A stirred mixture of 4-methyl-3-oxo-5α-4-azaandrostan-17-carboxaldehyde (0.952 g, 3.0 mM), hydroxylamine hydrochloride (1.10 g, 15.8 mM), anhydrous pyridine (6 mL) and anhydrous ethanol (12 mL) was refluxed gently under a nitrogen atmosphere for 6.3 hours. After cooling, the ice-cooled mixture was diluted, with stirring, with a slight excess of chilled dilute hydrochloric acid (ca. 0.3N), the suspension aged for ca. 20 minutes, filtered, washed with water and dried to give (1) 0.855 g. MS M$^+$ calcd for $C_{20}H_{32}N_2O_2$ 332.48, observed m/e 332.

Synthesis of Reactant 4-Azasteroid Amines

EXAMPLES 2–9

2) 17-Aminomethyl-4-methyl-5α-4-azaandrostan-3-one

A mixture of (1) (0.67 g, 2.0 mM), ethanol (100 mL), glacial acetic acid (8 mL) and water (4 mL) was reduced in a hydrogen atmosphere (40 p.s.i.) at room temperature in the presence of $PtO_2$ until TLC analysis indicated complete reduction. The filtered reaction mixture was concentrated in vacuo, the residue taken up in chloroform, and the chloroform solution washed with fresh dilute sodium hydrogen carbonate solution and dried ($Na_2SO_4$). Concentration of the filtered chloroform solution followed by trituration of the residue obtained with hexane containing a small amount of ether yielded (2) as an off-white solid.

MS MH$^+$ calcd for $C_{20}H_{34}N_2O$ 318.49, observed m/e 319.

The following amines are representative of those obtained from the corresponding carbonyl compounds utilizing the above procedures:

3) 17-Aminomethyl-5α-4-azaandrostan-3-one.

4) 17-Amino-4-methyl-5α-4-azaandrostane-3-one.

5) 17-Amino-5α-4-azaandrostan-3-one.

6) 20-Amino-4-methyl-5α-4-azapregnan-3-one.

7) 20-Amino-5α-4-azapregnan-3-one.

8) 20-(Aminomethyl)-4-methyl-5α-4-azapregnan-3-one.

9) 20-(Aminomethyl)-5α-4-azapregnan-3-one.

Synthesis of Ureido 4-Azasteroids

EXAMPLES 10–13

10) 17-(N'-t-Butylureidomethyl)-4-methyl-5α-4-azaandrostan-3-one

To a stirred solution of (2) (0.064 g, 0.2 mM) in dry benzene (8 mL) at room temperature was added t-butyl isocyanate (0.035 mL, 0.3 mM) dropwise over ca. 0.5 min. After stirring overnight the benzene was removed in vacuo and the residue flash chromatographed (silica gel, ethyl acetate as eluant) to give (10) as a white solid.

MS M$^+$ calcd for $C_{25}H_{43}N_3O_2$ 417.64, observed m/e 417.

11) 17-(N'-t-Butylureido)-4-methyl-5α-4-azaandro-stan-3-one

When (2) in the above example was replaced by (4), (11) was obtained as a white solid.

MS M$^+$ calcd for $C_{24}H_{41}N_3O_2$ 403.61, observed m/e 405.

12) 4-Methyl-20-(N'-methylureido)-5α-4-azapregnan-3-one

When (6) was reacted with methyl isocyanate under the conditions of Example (10), (12) was obtained as a white waxy solid.

MS M$^+$ calcd for $C_{23}H_{39}N_3O_2$ 389.58, observed m/e 389.

13) 4-Methyl-17-(N'-phenylureidomethyl)-5α-4-azaandrostan-3-one

When (2) was reacted with phenyl isocyanate under the conditions of Example (10), (13) was obtained as a white solid.

MS MH$^+$ calcd for $C_{27}H_{39}N_3O_2$ 437.40, observed m/e 438.

Examples 14–21 prepared according to the basic procedures described above further exemplify the claimed invention.

14) 4-Methyl-17β-(N'-n-propylureidomethyl)-5α-4-azaandro-stan-3-one

MS MH$^+$ calc. for $C_{24}H_{41}N_3O_2$ 403.40, observed m/e 404.

15) 4-Methyl-17β-(N'-n-octylureidomethyl)-5α-4-azaandrostan-3-one

MS MH$^+$ calc. for $C_{29}H_{51}N_3O_2$ 473.49, observed m/e 474.

16) 4-Methyl, 17β-(N'-phenylureido)-5α-4-azaandrostan-3-one

MS MH$^+$ calc. for $C_{26}H_{37}N_3O_2$ 423.52, observed m/e 424.

17) 17β-(N'-Isopropylureidomethyl)-4-methyl-5α-4-azaandrostan-3-one

MS MH$^+$ calcd for $C_{24}H_{41}N_3O_2$ 403.61 observed m/e 404.

18) 20-(N'-t-Butylureidomethyl)-4-methyl-5α-4-azapregnan-3-one

MS MH$^+$ calcd for $C_{27}H_{47}N_3O_2$ 445.35, observed m/3 446.

19) 20-((Iminodibenz-5-yl)carbonylaminomethyl)-4-methyl-5α-4-azapregnan-3-one

MS MH$_2^{++}$ calcd. for $C_{37}H_{49}N_3O_2$ 567.82, observed m/e 569.

20) 17β-((Iminodibenz-5-yl)carbonylaminomethyl)-4-methyl-5α-4-azaandrostan-3-one MS MH$_2^{++}$ calcd. for $C_{35}H_{45}N_3O_2$ 539.74, observed m/e 541.

21) 17β-((Isobutyloxycarbonylaminomethyl)-4-methyl-5α-4-azaandrostan-3-one

MS MH$^+$ calcd. for $C_{25}H_{42}N_2O_3$ 418.62, observed m/e 419.

Table 2 illustrates the NMR data of the above examples.

TABLE 2

| Example | NMR DATA (ppm) | |
|---|---|---|
| | Angular Methyls | Miscellaneous |
| 10 | 0.66, 0.86 | 1.33 (—NHCONH—C(C$\underline{H}_3$)$_3$) |
| 11 | 0.67, 0.99 | 1.33 (—NHCONH—C(C$\underline{H}_3$)$_3$) |
| 12 | 0.73, 0.98 | 2.92 (-4-NC$\underline{H}_3$) |
| 13 | 0.64, 0.86 | 2.92 (-4-NC$\underline{H}_3$) |
| 14 | 0.64, 0.99 | 2.90 (-4-NC$\underline{H}_3$) |
| 16 | 0.63, 0.96 | 2.93 (-4-NC$\underline{H}_3$) |
| 17 | 0.66, 0.88 | 1.12 (-NH-CH(C$\underline{H}_3$)$_2$ 1.16 |
| 18 | 0.64, 0.95 | 1.29 (—NHCONH—C(C$\underline{H}_3$)$_3$) |
| 19 | 0.62, 0.89 | 0.82 —CH(C$\underline{H}_3$)CH$_2$NHCON— 0.86 |
| 20 | 0.61, 0.88 | 2.92 (-4-NC$\underline{H}_3$) |
| 21 | 0.66, 0.88 | 2.92 (-4-NC$\underline{H}_3$) |

In addition to the compounds described above the following compounds were also prepared according to the processes described in the specification:

17β-(N'(Adamant-1-yl)thioureidomethyl)-4-methyl-5-α-4-azaandrostan-3-one,

17β-((1-Adamantyloxy)-carbonylaminomethyl)-5-α-4-methyl-4-azaandrostan-3-one, and 4-Methyl-17β-(N'-(4-(trifluromethoxy)phenyl))-5-α-4-azaandrostan-3one. The 1-en-3-one compounds of each of the above examples and of the claimed compounds may readily be prepared according to well known synthetic processes.

The above examples are non-limiting and suitable acylating agents, isocyanates, or thioisocyanates may readily be substituted according to the methods described in the present invention and reacted with a described azasteroidal amine to form the claimed ureas, thioureas, carbamates, and thiocarbamates. The following definitions further clarify the present invention.

The term "pharmaceutically acceptable salts" shall mean non-toxic salts of the compounds of this invention which are generally prepared by the free base with a suitable organic or inorganic acid. Representative salts include the following salts: Acetate, adipate, alginate, aspartate, benzenesulfonate, benzoate, bicarbonate, bisulfate, borate, butyrate, camsylate, carbonate, camphorate, chloride, citrate, fumarate, glucoheptanate, gluconate, glutamate, glycerolphosphate, hydrobromide, hydrochloride, hydroiodide, tactate, laurate, malate, maleate, mandelate, mesylate, methylbromide, methylnitrate, methylsulfate, mucate, napsylate, nitrate, oleate, oxalate. The invention further relates to all stereoisomers, diastereomers or enantiomers of the compounds depicted.

The term "pharmaceutically effective amount" shall mean that amount or quantity of a drug or pharmaceutical agent that will elicit the biological or medical response of a tissue, system or animal that is being sought by a reseacher or clinician or physician.

The term "aryl" shall mean a mono- or polycyclic system composed of 6-membered aromatic rings either unsubstituted or substituted with R wherein R is defined as H, $C_{1-6}$ alkyl or aryl$C_{1-20}$alkyl wherein said alkyl groups are unsubstituted or substituted with $C_{1-8}$ alkyloxy, amino, mono- and di -$C_1$-$C_4$ alkylamino, $C_1$-$C_4$ alkylthio, $C_1$-$C_4$ alkylsulfinyl, $C_1$-$C_4$ alkylsulfinyl, carboxy$C_{1-10}$alkyl, hydroxy, or halogen. The term "aryl" also encompasses those aromatic systems which independently have $C_{1-20}$alkyl, hydroxyl, $C_{1-20}$ alkyloxy, halo$C_{1-20}$alkyl, benzoyl, cyano, nitro, carboxamido, acetamido, $C_{2-20}$alkenyl and halogens directly bonded to the aromatic carbon atom(s) or as further defined in the specification. The term aryl specifically includes phenyl, napthyl, and anthrancenyl or biphenyl.

The term "heteroaryl" shall mean a mono- or polycyclic system composed of 5- and 6-membered aromatic rings containing 1,2,3 or four heteroatoms chosen from N, O, or S and either unsubstituted or substituted with R as defined above or with hydroxyl, $C_{1-20}$alkyloxy. $C_{1-20}$alkyl, $C_{2-20}$alkenyl, halo$C_{1-20}$alkyl, benzoyl, cyano, nitro, carboxamido, acetamido and halogens directly bonded to the aromatic carbon atoms. The term heteroaryl is further defined to include heterocyclic species such as 5–7-membered monocyclic rings which are either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring so that a portion of the molecule is aromatic. Examples of heterocyclic species or elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiszolidinyl, indolyl, quinolinyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Preferred embodiments clearly include those heteroaryl and heterocyclic species depicted in the specific examples.

The term "alkyl" shall mean straight or branched chain alkane.

The term "alkenyl" shall mean straight or branched chain alkene.

The term "alkynyl" shall mean straight or branched chain alkyne.

The term "arylalkyl" shall be taken to include an aryl portion as defined above and an alkyl portion as defined above.

The term "heteroarylalkyl" shall mean an heteroaryl portion as defined above and an alkyl portion as defined above.

The "$C_{1-n}$" designation where n may be an integer from 1 to 20 or 2–20 respectively refers to an alkyl group or substituent and to the alkyl portion of an arylalkyl or heteroarylalkyl unit. In addition, it refers to cycloalkyl substituents and alkenyl, aryl or alkynyl groups.

The term "halogen" shall include fluorine, chlorine, iodine and bromine.

The term "oxy" shall mean an oxygen (O) atom.

The term "thio" shall mean a sulfur atom.

In the schemes and examples described in this disclosure, various reagent symbols have the following meanings:

$PtO_2$ is platinum oxide
TLC is thin layer chromatography
$Na_2SO_4$ is sodium sulfate
DMAP is 4-(dimethylamino)pyridine
DCC is N,N'-dicyclohexylcarbodiimide, The previous examples are illustrative of representative embodiments of this invention and should not be construed to be limits on the scope or spirit of the instant invention.

The Rf values cited were carried out on standard thin layer chromatographic silica gel plates. The elution solvent system used is given in the parentheses following the Rf value.

The mass spectral values are given either as FAB, i.e., fast atom bombardment, or electron impact (EI) and are reported as molecular ion peaks, either being (M). (M+1) or (M+2), the molecular weight, MW, or the MW plus one or two atomic units.

The nuclear magnetic resonance data was then at 200 or 400 MHz in $CDCl_3$ and is tabulated for unique proton values of each compound at the end of the Examples.

Also included within the scope of this invention are 4—N—X analogs where X is OH, $NH_2$ or $SCH_3$. The 4—N—OH and 4—N—$NH_2$ derivatives can be made by incorporating hydroxylamine or hydrazine, respectively, in place of methylamine in the seco acid ring A closure for the starting androstanes herein described in J. Med. Chem. 29, 2998–2315 (1986) by Rasmusson et al. Futher, reaction of the anion of the saturated 4—N—H adrostanes, wherein the anion is generated from the 4—N—H precursor by sodium hydride, and methylsulfenyl chloride can produce the corresponding 4—N—S—$CH_3$ derivetive. Thus, substituent R or the 4-N position also include, OH, $NH_2$ and S—$CH_3$.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/ per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5 α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient: and the particular compound or salt thereof employed. An ordinarily skilled physician or veterinarian can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range between about Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxidepolyllysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

BIOLOGICAL ASSAYS

Preparation of Human Prostatic and Scalp
5a-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase Assay

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C—T (or $^{3}$H—T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler. Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail Macaque Protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)
3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximatly 250 μL of vehicle and 5α-reductase in vehicle is prepared and topically administered to the tatooed area of the scelp. The selected 5α-reductase and placebo is ingested by the monekys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at $p<0.05$. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula:

(I)

and the pharmaceutically acceptable salts thereof, wherein:

A is:

$$R^4\diagdown N-\underset{\underset{|}{R^2}}{\overset{\overset{Y}{\|}}{C}}-Z-R^3, \quad (a)$$

$$R^2\diagdown \underset{|}{N}-\overset{\overset{O}{\|}}{C}-O-R^3, \text{ or} \quad (b)$$

$$R^4\diagdown (CH)_x-\underset{\underset{|}{R^2}}{\overset{\overset{Y}{\|}}{N}-\overset{\overset{R^6}{|}}{C}}-Z-R^3; \quad (c)$$

wherein
$R^1$ is:
 H, methyl or ethyl;
$R^2$ is:
 H, or
 $C_{1-3}$ alkyl;
$R^3$ is:
 H,
 amino,
 mono $C_1$-$C_4$ alkylamino,
 di $C_1$-$C_4$ alkylamino,
 mono $C_1$-$C_4$ alkylaminoaryl,
 di $C_1$-$C_4$ alkylaminoaryl,
 $C_{1-20}$ alkyl,
 aryl,
 heteroaryl,
 aryl $C_{1-20}$ alkyl,
 $C_{3-20}$ cycloalkyl,
 $C_{3-20}$ cycloalkyl $C_{1-20}$alkyl,
 heteroaryl $C_{1-20}$alkyl,
 $C_{2-20}$ alkenyl $C_{1-20}$alkyl,
 halo $C_{1-20}$ alkyl,
 $C_{1-20}$ alkyloxycarbonyl $C_{1-20}$ alkyl,
 $C_{1-20}$ alkyloxy $C_{1-20}$ alkyl,
 carboxy $C_{1-20}$ alkyl,
 arylcarbonyl aryl $C_{1-20}$ alkyl,
 $C_{1-20}$ alkylcarbonyl $C_{1-20}$ alkyl,
 aryl $C_{1-20}$ alkyloxycarbonyl $C_{1-20}$ alkyl,
 heteroaryl $C_{1-20}$ alkyloxycarbonyl $C_{1-20}$ alkyl,
 hydroxyl $C_{1-20}$ alkyl,
 halohydroxyl $C_{1-20}$ alkyl,
 aryl $C_{1-20}$ alkyloxy $C_{1-20}$ alkyl,
 heteroaryl $C_{1-20}$ alkyloxy $C_{1-20}$ alkyl,
 carboxyl $C_{1-20}$ alkyl,
 thiosulfato $C_{1-20}$ alkyl diaryl $C_{1-20}$ alkyl of the formula:

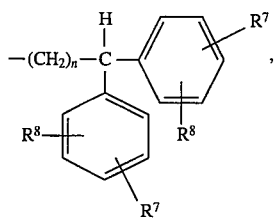

n equals 0–19;
triaryl $C_{1-20}$ alkyl of the formula

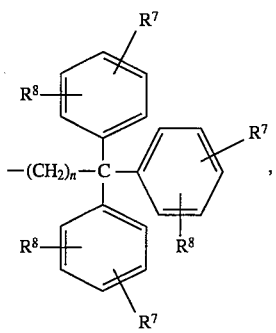

n equals 1–19;
$C_{2-20}$ alkenyl,
$C_{2-20}$ alkenyl $C_{1-20}$ alkyl,
$C_{2-20}$ alkynyl $C_{1-20}$ alkyl,
aryl $C_{2-20}$ alkynyl $C_{1-20}$ alkyl,
heteroaryl $C_{2-20}$ alkynyl $C_{1-20}$ alkyl,
$C_{1-20}$ alkylthio $C_{1-20}$ alkyl,
$C_{1-20}$ alkylsulfonyl $C_{1-20}$ alkyl, or
$C_{1-20}$ alkylsulfinyl $C_{1-20}$ alkyl;
wherein aryl is either unsubstituted for mono- or di-substituted with
R',
wherein R' is selected from H, $C_{1-20}$ alkyl, hydroxyl, $C_{1-20}$ alkyloxy, halo $C_{1-20}$ alkyl, benzoyl, cyano, nitro, carboxamido, acetamido, $C_{2-20}$ alkenyl, halogen, and aryl $C_{1-20}$ alkyl,
wherein said alkyl is unsubstituted or substituted with one of $C_{1-8}$ alkyloxy, amino, mono $C_{1-4}$ alkylamino, di $C_{1-4}$ alkylamino, $C_{1-4}$ alkylthio, $C_{1-4}$ alkylsulfinyl, $C_{1-4}$ alkylsulfonyl, carboxy $C_{1-10}$ alkyl, hydroxy, or halogen;

$R^4$ is:
H,
$C_{1-20}$ alkyl,
aryl, either unsubstituted or substituted with one or R,
wherein R is H, $C_{1-6}$ alkyl, aryl $C_{1-20}$ alkyl with the alkyl groups unsubstituted or substituted with one of hydroxyl, $C_{1-8}$ alkyloxy, carboxy $C_{0-10}$ alkyl, or halogen or aryl directly substituted independently with one of amino, mono $C_{1-4}$ alkylamino, di $C_{1-4}$ alkylamino, mono $C_{1-4}$ alkylaminoaryl, di $C_{1-4}$ alkylaminoaryl, hydroxyl, halo $C_{1-20}$ alkyl, carboxamido, benzoyl, $C_{1-20}$ alkyloxy, $C_{1-20}$ alkyl, $C_{2-20}$ alkenyl, cyano, nitro, acetamide or halogen, or;
heteroaryl;

$R^5$ can be the same or different when x is greater than 1 and is:
H,
$C_{1-12}$ alkyl,
heteroaryl, or
aryl;
wherein aryl is either unsubstituted or substituted with one of R',
wherein R' is selected from H, $C_{1-20}$ alkyl, hydroxyl, $C_{1-20}$ alkyloxy, halo $C_{1-20}$ alkyl, benzoyl, cyano, nitro, carboxamido, acetamido, $C_{2-20}$ alkenyl, halogen, and aryl $C_{1-20}$ alkyl,
wherein said alkyl is unsubstituted or substituted with one of $C_{1-8}$ alkyloxy, amino, mono $C_{1-4}$ alkylamino, di $C_{1-4}$ alkylamino, $C_{1-4}$ alkylthio, $C_{1-4}$ alkylsulfinyl, $C_{1-4}$ alkylsulfonyl, carboxy $C_{1-10}$ alkyl, hydroxy, or halogen;

$R^6$ is present when Z equals N and is independently
H,
$C_{1-20}$ alkyl, or
equivalent to $R^3$; or taken together with $R^3$ and the N to which they are attached represents a monocyclic mono N heteroaryl;

$R^7$ and $R^8$ are independently selected from:
H,
$CH_3$,
$C_2H_5$,
carboxamido,
OH,
$OCH_3$,
$NO_2$,
CN,
F,
RS,
RSO,
$RSO_2$,
$R_2N$, where R can be the same or different selected from H, $C_{1-4}$ alkyl, or aryl;
Cl,
acetamido,
$OC_2H_5$,
$CF_3$,
isopropyl, and
isobutyl, n equals 1–10 and the $C_{1-20}$ alkyl portion is optionally substituted with $R^5$;

Y is:
O, or
S;
Z is:
N, or
O;
x is an integer from 1–25;
at each occurrence, aryl is phenyl;
at each occurrence, heteroaryl is independently selected from pyrrolyl, imidazolyl pyrazolyl, pyridyl, oxazolyl, isoxazolyl, thiazolyl, isothiazolyl, indolyl, quinolinyl, isoquinolinyl, benzimidazolyl, thiadiazolyl, benzopyranyl, benzothiazolyl, benzoxazolyl, furyl, thienyl, benzothienyl, benztriazolyl and oxadiazolyl;
and dashes indicate a double bond is optionally present.

2. A compound according to claim 1 and the pharmaceutically acceptable salts thereof, wherein:
A is:

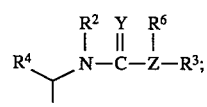

$R^1$ is:

H, methyl or ethyl:
R² is:
H, or
C₁₋₃ alkyl;
R³ is:
H,
C₁₋₂₀ alkyl,
aryl C₁₋₂₀ alkyl,
C₃₋₂₀ cycloalkyl,
C₃₋₂₀ cycloalkyl C₁₋₂₀alkyl.
heteroaryl C₁₋₂₀alkyl,
C₁₋₂₀ alkylcarbonyl C₁₋₂₀ alkyl,
aryl C₁₋₂₀ alkyloxycarbonyl C₁₋₂₀ alkyl,
carboxyl C₁₋₂₀ alkyl,
heteroaryl C₁₋₂₀ alkyloxycarbonyl C₁₋₂₀ alkyl,
hydroxyl C₁₋₂₀ alkyl,
aryl C₁₋₂₀ alkyloxy C₁₋₂₀ alkyl,
heteroaryl,
aryl,
C₁₋₂₀ alkyloxycarbonyl C₁₋₂₀ alkyl,
C₂₋₂₀ alkenyl C₁₋₂₀alkyl
C₁₋₂₀ alkyloxy C₁₋₂₀ alkyl,
arylcarbonyl aryl C₁₋₂₀ alkyl,
halohydroxyl C₁₋₂₀ alkyl,
diaryl C₁₋₂₀ alkyl of the formula:

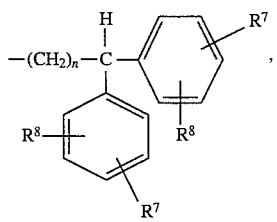

n equals 0–19;
triaryl C₁₋₂₀ alkyl of the formula

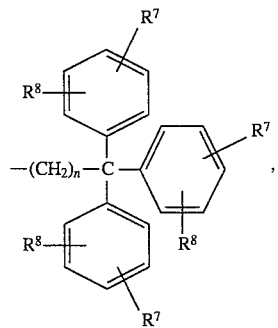

n equals 1–19:
halo C₁₋₂₀ alkyl,
C₁₋₂₀ alkyloxy C₁₋₂₀ alkyl,
C₁₋₂₀ alkylthio C₁₋₂₀ alkyl,
C₁₋₂₀ alkylsulfonyl C₁₋₂₀ alkyl, or
C₁₋₂₀ alkylsulfinyl C₁₋₂₀ alkyl;
wherein aryl is phenyl unsubstituted or substituted with one of R', as defined in claim 1;
R⁴ is:
H,
C₁₋₂₀ alkyl,
heteroaryl, or
aryl, either unsubstituted or substituted with R, wherein R is H, C₁₋₆ alkyl, aryl C₁₋₂₀ alkyl with the alkyl groups unsubstituted or substituted with one of hydroxyl, C₁₋₈ alkyloxy, carboxy C₀₋₁₀ alkyl, or halogen or aryl directly substituted independently with one of amino, mono C₁₋₄ alkylamino, diC₁₋₄ alkylamino, mono C₁₋₄ alkylaminoaryl, di C₁₋₄ alkylaminoaryl, hydroxyl, halo C₁₋₂₀ alkyl, carboxamido, benzoyl, C₁₋₂₀ alkyloxy, C₁₋₂₀ alkyl, C₂₋₂₀ alkenyl, cyano, nitro, acetamide or halogen;
R⁶ is present when Z equals N and is independently
H,
C₁₋₂₀ alkyl, or
equivalent to R³; or taken together with R³ and the N to which they are attached represents a monocyclic mono N heteroaryl;
R⁷ and R⁸ are independently selected from:
H,
CH₃,
C₂H₅,
carboxamido,
OH,
OCH₃,
NO₂,
CN,
F,
RS,
RSO,
RSO₂,
R₂N, where R can be the same or different selected from H, C₁₋₄ alkyl, or aryl;
Cl,
acetamido,
OC₂H₅,
CF₃,
isopropyl, and
isobutyl; n equals 1–10 and the C₁₋₂₀ alkyl portion is optionally substituted with one of R⁵;
Y is:
O, or
S;
Z is: N, or
O.
3. A compound according to claim 2 and the pharmaceutically acceptable salts thereof wherein:
R¹ is:
H,
CH₃, or
C₂H₅;
R² is:
H,
CH₃, or
C₂H₅, or linear or branched;
C₃H₇;
R³ is:
-t-butyl
3-thienyl
2-thienyl,
-11-(isopropylthio)undecyl,
-7-(carbomethoxy)heptyl,
-(4-isobutylbenzene)ethyl,
-7-(carboxy)heptyl,
-acetylmethyl,
-1-adamantylmethyl,
-2-thienylmethyl,
-2-(carbobenzyloxy)ethyl,
-3,4-dimethoxyphenylmethyl,
-phenyl,
-5-bromopentyl,
-11-hydroxyundecyl, -1(4-nitrophenyl)ethyl,
-isopropylthiomethyl,
-benzyloxymethyl,
-carbomethoxymethyl,
-diphenylmethyl,
-triphenylmethyl,
-2-furyl,
4-isopropylphenyl,
cyclohexylmethyl,
4-methylcyclohexyl,
3-(3-indolyl)propyl,
3-indolylmethyl,
4-isobutylbenzyl,
4-nitrobenzyl,
3-acetamidomethyl,
4-ethoxybenzyl,
hexadecyl,
stearyl,
3,5-bis(trifluoromethyl),
3-cyanobenzyl,
heptafluoropropyl,
4-benzoylbenzyl,
5-benztriazolyl,
3,5-diflourobenzyl,
bis(4-isopropylphenyl)methyl,
2 hydroxybenzyl,
methyl,
allyl,
n-propyl,
n-octyl,
isopropyl,
isobutyl,
ethyl,
benzyl,
octadecyl,
2(ethyl)phenyl,
3(chloro)phenyl,
4(methyl)phenyl,
2,3(dichloro)phenyl,
4(fluoro)phenyl,
3(methoxy)phenyl,
2(ethoxy)phenyl,
or
2- thiazolyl;

$R^4$ is:
H,
methyl,
ethyl,
linear or branched:
propyl,
butyl,
aryl, either unsubstituted or substituted with one of R, wherein R is H, $C_{1-6}$ alkyl, aryl $C_{1-20}$ alkyl with the alkyl groups unsubstituted or substituted with one of hydroxyl, $C_{1-8}$ alkyloxy, carboxy $C_{0-10}$ alkyl, or halogen or aryl directly substituted independently with one of amino, mono $C_{1-4}$ alkylamino, di $C_{1-4}$ alkylamino, mono $C_{1-4}$ alkylaminoaryl, di $C_{1-4}$ alkylaminoaryl, hydroxyl, halo $C_{1-20}$ alkyl, carboxamido, benzoyl, $C_{1-20}$ alkyloxy, $C_{1-20}$ alkyl, $C_{2-20}$ alkenyl, cyano, nitro, acetamide or halogen, or heteroaryl;

$R^6$ is present when Z equals N and is independently
H,
$C_{1-20}$ alkyl, or
equivalent to $R^3$; or taken together with $R^3$ and the N to which they are attached represents a monocyclic mono N heteroaryl;

Y is:
O, or
S;

Z is:
N, or
O.

4. The compound according to claim 3 and the pharmaceutically acceptable salts thereof, wherein the compound is selected from:

17β-(N'-t-Butylureidomethyl)-4-methyl-5-α-4-azaandrostan-3-one,

4-Methyl-17β-(N'-phenylureidomethyl-5α-4-azaandrostan-3-one,

4-Methyl-20-(N'-methylureido)-5α-4-azapregnan-3-one,

4-Methyl-17β-(N'-n-propylureidomethyl-5-α-4-azaandrostan-3-one,

4-Methyl-17β-(N'-n-octylureidomethyl)-5-α-4-azaandrostan-3-one,

17β-(N'-isopropylureidomethyl)-4-methyl-5α-4-azaandrostan-3-one,

17β-(isobutyloxycarbonylaminomethyl)-4-methyl-5α-4azaandrostan- 3-one, 20-(Ethoxycarbonylamino)-4-methyl-5α-4-aza-pregnan-3-one, 4-Methyl-17β-(N'-octadecylureidomethyl)-5α-4-azaandrostan-3-one, 17β-(N'-(2-Ethylphenyl)ureidomethyl)-5α-4-azaandrostan-3-one, 20-(N'-(3-Chlorophenyl)ureido)-5α-4-azapregnan-an-3-one, 4-Methyl-20-(N'-phenylureido)-5α-4-azapregnan-3-one, 17β-(N'-(2'3,-Dichlorophenyl)ureidomethyl)-4-methyl-5α-4 azaandrostan-3-one, 4-Methyl-17β(N'-thiazol-2-ylureidomethyl)-5α-4-azaandrostan-3-one.

5. The compound according to claim 3 and the pharmaceutically acceptable salts thereof, wherein the compound is selected from:

17β-(N'-t-Butylureidomethyl)-4-methyl-5-α-4-azaandrost-1-en-3-one,

4-Methyl-17β-(N'-phenylureidomethyl-5α-4-azaandrostl-en-3-one,

4-Methyl-20-(N'-methylureido)-5α-4-azapreg-1-en-3-one,

4-Methyl-17β-(N'-n-propylureidomethyl-5-α-4-aza-androst-1-en-3-one,

4-Methyl-17β-(N'-n-octylureidomethyl)-5-α-4-azaandrost-1-en-3-one,

17β-(N'-isopropylureidomethyl)-4-methyl-5α-4-azaandrost-1-en-3-one,

17β-(isobutyloxycarbonylaminomethyl)-4-methyl-5α-4-azaandrost-1-en-3-one, 20-(Ethoxycarbonylamino)-4-methyl-5α-4-aza-preg-1-en-3-one, 4-Methyl-17β-(N'-octadecylureidomethyl)-5α-4-azaandrost-1-en-3-one, 17β-(N'-(2-Ethylphenyl)ureidomethyl)-5α-4-azaandrost-1-en-3-one, 20-(N'-(3-Chlorophenyl)ureido)-5α-4-azapreg-1-en-3-one, 4-Methyl-20-(N'-phenylureido)-5α-4-azapreg-1-en-3-one, 17β-(N'-(2'3,-Dichlorophenyl)ureidomethyl)-4-methyl-5α-4-azaandrost-1-en-3-one, 4-Methyl-17β(N'-thiazol-2-ylureidomethyl)-5α-4-aza-androst-1-en-3-one, 17β-((1-Adamantyloxy)-carbonylaminomethyl)-5-α-4-methyl-4-azaandrostan-1-en-3-one, or 4-Methyl-20-(N'-thien-2-ylmethylureido)-5α-4-azapreg-1-en-3-one.

6. A compound according to claim 1 and the pharmaceutically acceptable salts thereof wherein:

A is

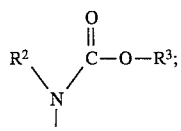

wherein
R¹ is:
  H, methyl or ethyl;
R² is:
  H, or
  $C_{1-3}$ alkyl;
R³ is:
  H,
  $C_{1-20}$ alkyl,
  aryl $C_{1-20}$ alkyl,
  $C_{3-20}$ cycloalkyl,
  $C_{3-20}$ cycloalkyl $C_{1-20}$alkyl,
  heteroaryl $C_{1-20}$alkyl,
  $C_{1-20}$ alkylcarbonyl $C_{1-20}$alkyl,
  aryl $C_{1-20}$ alkyloxycarbonyl $C_{1-20}$alkyl,
  carboxy $C_{1-20}$alkyl,
  heteroaryl $C_{1-20}$ alkyloxycarbonyl $C_{1-20}$ alkyl,
  hydroxyl $C_{1-20}$ alkyl,
  aryl $C_{1-20}$ alkyloxy $C_{1-20}$ alkyl,
  heteroaryl,
  aryl,
  $C_{1-20}$ alkyloxycarbonyl $C_{1-20}$ alkyl,
  arylcarbonylaryl $C_{1-20}$ alkyl
  halohydroxyl $C_{1-20}$ alkyl,
  diaryl $C_{1-20}$ alkyl,
  triaryl $C_{1-20}$ alkyl,
  $C_{2-20}$ alkenyl $C_{1-20}$ alkyl,
  halo $C_{1-20}$ alkyl,
  $C_{1-20}$ alkyloxy $C_{1-20}$ alkyl,
  $C_{2-20}$ alkenyl $C_{1-20}$ alkyl,
  $C_{1-20}$ alkylthio $C_{1-20}$ alkyl,
  $C_{1-20}$ alkylsulfonyl $C_{1-20}$ alkyl, or
  $C_{1-20}$ alkylsulfinyl $C_{1-20}$ alkyl;
  wherein aryl is phenyl unsubstituted or substituted with one of R', as defined in claim 1.

7. A compound according to claim 6 and the pharmaceutically acceptable salts thereof wherein:
R¹ is:
  H, methyl or ethyl:
R² is:
  H, or
  $C_{1-3}$ alkyl;
R³ is:
  -t-butyl
  3-thienyl
  2-thienyl,
  -11-(isopropylthio)undecyl,
  -7-(carbomethoxy)heptyl,
  -(4-isobutylbenzene)ethyl,
  -7-(carboxy)heptyl,
  -acetylmethyl,
  -1-adamantylmethyl,
  -2-thienylmethyl,
  -2-(carbobenzyloxy)ethyl,
  -3,4-dimethoxyphenylmethyl,
  -phenyl,
  -5-bromopentyl,
  11-hydroxyundecyl,
  -1(4-nitrophenyl)ethyl,
  -isopropylthiomethyl,
  -benzyloxymethyl,
  -carbomethoxymethyl,
  -diphenylmethyl,
  -triphenylmethyl,
  -2-furyl,
  4-isopropylphenyl,
  cyclohexylmethyl,
  4-methylcyclohexyl,
  3-(3-indolyl)propyl,
  3-indolylmethyl,
  4-isobutylbenzyl,
  4-nitrophenylbenzyl,
  3-acetamidomethyl,
  4-ethoxybenzyl,
  hexadecyl,
  stearyl,
  3,5-bis(trifluoromethyl),
  3-cyanobenzyl,
  heptafluoropropyl,
  4-benzoylbenzyl,
  5-benztriazolyl,
  3,5-difluorobenzyl,
  bis(4-isopropylphenyl)methyl,
  2 hydroxybenzyl,
  methyl,
  allyl,
  n-propyl,
  n-octyl,
  isopropyl,
  isobutyl,
  ethyl,
  benzyl,
  octadecyl,
  2(ethyl)phenyl,
  3(chloro)phenyl,
  4(methyl)phenyl,
  2,3(dichloro)phenyl,
  4(fluoro)phenyl,
  3(methoxy)phenyl,
  2(ethoxy)phenyl,
  or
  2-thiazolyl.

8. A compound according to claim 1 and the pharmaceutically acceptable salts thereof, wherein:

A is:

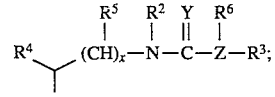

wherein
R¹ is:
  H, methyl or ethyl;

47

$R^2$ is:
  H, or
  $C_{1-3}$ alkyl;
$R^3$ is:
  H,
  $C_{1-20}$ alkyl,
  aryl $C_{1-20}$ alkyl,
  $C_{3-20}$ cycloalkyl,
  $C_{3-20}$ cycloalkyl $C_{1-20}$ alkyl,
  heteroaryl $C_{1-20}$ alkyl,
  $C_{1-20}$ alkylcarbonyl $C_{1-20}$ alkyl,
  aryl $C_{1-20}$ alkyloxycarbonyl $C_{1-20}$ alkyl,
  carboxyl $C_{1-20}$ alkyl,
  heteroaryl $C_{1-20}$ alkyloxycarbonyl $C_{1-20}$ alkyl,
  hydroxyl $C_{1-20}$ alkyl,
  aryl $C_{1-20}$ alkyloxy $C_{1-20}$ alkyl,
  heteroaryl,
  aryl,
  $C_{1-20}$ alkyloxycarbonyl $C_{1-20}$ alkyl,
  $C_{2-20}$ alkenyl $C_{1-20}$ alkyl,
  $C_{1-20}$ alkyloxy $C_{1-20}$ alkyl,
  arylcarbonyl aryl $C_{1-20}$ alkyl,
  halohydroxyl $C_{1-20}$ alkyl,
  diaryl $C_{1-20}$ alkyl of the formula:

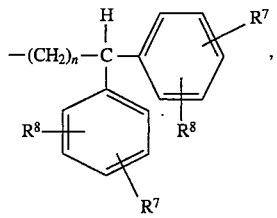

n equals 0–19; triaryl $C_{1-20}$ alkyl of the formula

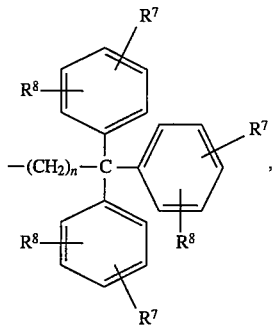

n equals 1–19;
  halo $C_{1-20}$ alkyl,
  $C_{1-20}$ alkyloxy $C_{1-20}$ alkyl,
  $C_{1-20}$ alkylthio $C_{1-20}$ alkyl,
  $C_{1-20}$ alkylsulfonyl $C_{1-20}$ alkyl, or
  $C_{1-20}$ alkylsulfinyl $C_{1-20}$ alkyl;
  wherein aryl is phenyl unsubstituted or substituted with one of R', as defined in claim 1;
$R^4$ is:
  $C_{1-20}$ alkyl,
  heteroaryl, or
  aryl either unsubstituted or substituted with one of R, wherein R is H, $C_{1-6}$ alkyl, aryl $C_{1-20}$ alkyl with the alkyl groups unsubstituted or substituted with one or hydroxyl, $C_{1-8}$ alkyloxy, carboxy $C_{0-10}$ alkyl, or halogen or aryl directly substituted independently with one of amino, mono $C_{1-4}$ alkylamino, di$C_{1-4}$ alkylamino, mono $C_{1-4}$ alkylaminoaryl, di$C_{1-4}$ alky-

48 laminoaryl, hydroxyl, halo $C_{1-20}$ alkyl, carboxamido, benzoyl, $C_{1-20}$ alkyloxy, $C_{1-20}$ alkyl, $C_{2-20}$ alkenyl, cyano, nitro, acetamide or halogen;
$R^6$ is present when Z equals N and is independently
  H,
  $C_{1-20}$ alkyl, or
  equivalent to $R^3$; or taken together with $R^3$ and the N to which they are attached represents a monocyclic mono N heteroaryl;
$R^7$ and $R^8$ are independently selected from:
  H,
  $CH_3$,
  $C_2H_5$,
  carboxamido,
  OH,
  $OCH_3$,
  $NO_2$,
  CN,
  F,
  RS,
  RSO,
  $RSO_2$,
  $R^2N$, where R can be the same or different selected from H, $C_1$-$C_4$ alkyl, or aryl;
  Cl,
  acetamido,
  $OC_2H_5$,
  $CF_3$,
  isopropyl, and
  isobutyl; n equals 1–10 and the $C_{1-20}$ alkyl portion is optionally substituted with $R^5$;
Y is:
  O, or
  S;
Z is:
  N, or
  O; and
x is an integer from 1–10.
9. A compound according to claim 8 and the pharmaceutically acceptable salts thereof wherein:
$R^1$ is:
  H, or methyl or ethyl;
$R^2$ is:
  H, or
  $C_{1-3}$ alkyl;
$R^3$ is:
  -t-butyl
  3-thienyl
  2-thienyl,
  -11-(isopropylthio)undecyl,
  -7-(carbomethoxy)heptyl,
  -(4-isobutylbenzene)ethyl,
  -7-(carboxy)heptyl,
  -acetylmethyl,
  -1-adamantylmethyl,
  -2-thienylmethyl,
  -2-(carbobenzyloxy)ethyl,
  -3,4-dimethoxyphenylmethyl,
  -phenyl,
  -5-bromopentyl,
  -11-hydroxyundecyl,
  -1(4-nitrophenyl)ethyl,
  -isopropylthiomethyl,
  -benzyloxymethyl,
  -carbomethoxymethyl,
  -diphenylmethyl, -triphenylmethyl,
-2-furyl,
4-isopropylphenyl,
cyclohexylmethyl,
4-methylcyclohexyl,
3-(3-indolyl)propyl,
3-indolylmethyl,
4-isobutylbenzyl,
4-nitrobenzyl,
3-acetamidomethyl,
4-ethoxybenzyl,
hexadecyl,
stearyl,
3,5-bis(trifluoromethyl),
3-cyanobenzyl,
heptafluoropropyl,
4-benzoylbenzyl,
5-benztriazolyl,
3,5-difluorobenzyl,
bis(4-isopropylphenyl)methyl,
2 hydroxybenzyl,
methyl,
allyl,
n-propyl,
n-octyl,
isopropyl,
isobutyl,
ethyl,
benzyl,
octadecyl,
2(ethyl)phenyl,
3(chloro)phenyl,
4(methyl)phenyl,
2,3(dichloro)phenyl,
4(fluoro)phenyl,
3(methoxy)phenyl,
2(ethoxy)phenyl, or
2-thiazolyl;

$R^4$ is:
H,
$C_{1-13}$ alkyl,
heteroaryl, or
aryl, either unsubstituted or substituted with one of R, wherein R is H, $C_{1-6}$ alkyl, aryl $C_{1-20}$ alkyl with the alkyl groups unsubstituted or substituted with one of hydroxyl, $C_{1-8}$ alkyloxy, carboxy $C_{0-10}$ alkyl, or halogen or aryl directly substituted independently with one of amino, mono $C_{1-4}$ alkylamino, di$C_{1-4}$ alkylamino, mono $C_{1-4}$ alkylaminoaryl, di$C_{1-4}$ alkylaminoaryl, hydroxyl, halo $C_{1-20}$ alkyl, carboxamido, benzoyl, $C_{1-20}$ alkyloxy, $C_{1-20}$ alkyl, $C_{2-20}$ alkenyl, cyano, nitro, acetamide or halogen;

$R^5$ can be the same or different when x is greater than 1 and is:
H, or
$C_{1-12}$ alkyl,
heteroaryl, or
aryl;

$R^6$ is present when Z equals N and is independently
H,
$C_{1-20}$ alkyl, or
equivalent to $R^3$; or taken together with $R^3$ and the N to which they are attached represents a monocyclic mono N heteroaryl;

Y is:
O, or
S;

Z is:
N, or
O;

x is an integer from 1–10.

10. The compound according to claim 9, wherein the compound is selected from:
20-(Benzyloxycarbonylaminomethyl)-5α-4-azapregnan-3-one,
20-(N'-p-tolylureidomethyl)-5α-4-azapregnan-3-one, or
20-(N'-(2-Ethoxyphenyl)ureidomethyl)-4-methyl-5α-4-azapregnan-3-one.

11. The compound according to claim 10, wherein the compound is selected from:
20-(N'-t-butylureidomethyl)-4-methyl-5α-4-azapreg-1-en-3-one,
20-((Iminodibenz-5-yl)carbonylaminomethyl)-4-methyl-5α-4-azapreg-1-en-3-one,
20-(Benzyloxycarbonylaminomethyl)-5α-4-azapreg-1-en-3-one,
20-(N'-p-tolylureidomethyl)-5α-4-aza-preg-1-en-3-one, or
20-(N'-(2-Ethoxyphenyl)ureidomethyl)-4-methyl-5α-4-azapreg-1-en-3-one.

12. A compound of the formula:

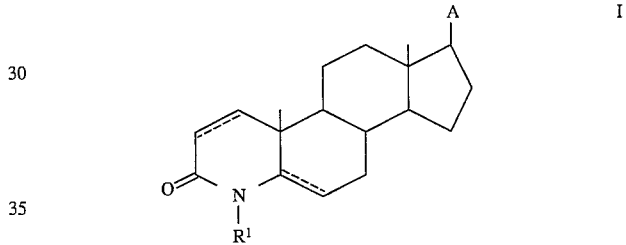

and the pharmaceutically acceptable salts thereof, wherein:
A is:

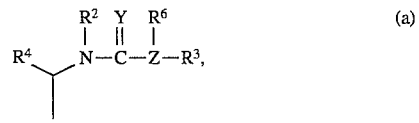 (a)

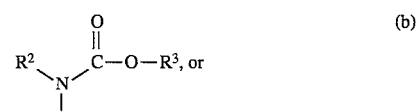 (b)

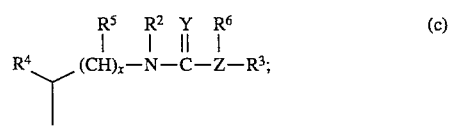 (c)

wherein
$R^1$ is:
H, methyl or ethyl;
$R^2$ is:
H, or
$C_{1-3}$ alkyl;
$R^3$ is:
H,
straight or branched chain $C_{1-20}$ alkyl,
aryl, either unsubstituted or mono- or di-substituted with R, wherein R is H, $C_{1-6}$ alkyl, aryl $C_{1-20}$ alkyl with the alkyl groups unsubstituted or substituted with one of hydroxyl, $C_{1-8}$ alkyloxy, carboxy $C_{0-10}$ alkyl, or halogen or aryl directly substituted independently with one of amino, mono $C_{1-4}$ alkylamino, di $C_{1-4}$ alkylamino, mono $C_{1-4}$ alkylaminoaryl, di $C_{1-4}$ alkylaminoaryl, hydroxyl, halo $C_{1-20}$ alkyl, carboxamido, benzoyl, $C_{1-20}$ alkyloxy, $C_{1-20}$ alkyl, $C_{2-20}$ alkenyl, cyano, nitro, acetamido or halogen, or;

heteroaryl, either unsubstituted or substituted with one of R or independently with hydroxyl $C_{1-20}$ alkyloxy, $C_{1-20}$ alkyl, benzoyl, carboxamolic, acetamide, halogens, $C_{2-20}$ alkenyl, cyano, nitro, or haloalkyl directly bonded to the aromatic carbon atom(s), aryl$C_{1-20}$alkyl or the formula:

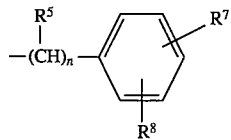

wherein the aromatic ring is optionally and independently substituted with $R_7$ and $R_8$ wherein $R_7$ and $R_8$ are selected from:
H,
$CH_3$,
$C_2H_5$,
carboxamido,
OH,
$OCH_3$,
$NO_2$,
CN,
F,
RS,
RSO,
$RSO_2$,
$R_2N$, where R can be the same or different selected from H, $C_{1-4}$ alkyl, or aryl;
Cl,
acetamido,
$OC_2H_5$,
$CF_3$,
isopropyl, and
isobutyl; n equals 1–10 and the $C_{1-20}$alkyl portion is optionally substituted with $R^5$;
heteroaryl$C_{1-20}$alkyl of the formula:

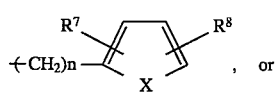, or

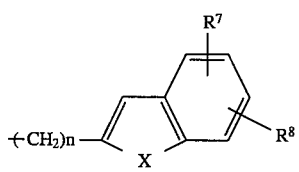

wherein X equals O, S, or NR; and n equals 1–20;
$C_{1-20}$alkylsulfonyl$C_{1-20}$alkyl,
$C_{1-20}$alkylthio$C_{1-20}$alkyl,
$C_{1-20}$alkylsulfinyl$C_{1-20}$alkyl of the formula:

—$(CH_2)nS(O)p$—$R^9$ wherein $R^9$ is $CH_3$,
$C_2H_5$,
$C_3H_7$,
$C_4H_9$,
isopropyl,
isobutyl,
sec-butyl,
t-butyl,
isopentyl,
neopentyl, or
isohexyl; n equals 1–15 and p=0–2;
$C_{1-20}$alkyloxycarbonyl$C_{1-20}$alkyl of the formula:

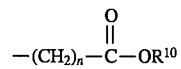

wherein $R^{10}$ is:
$CH_3$,
$C_2H_5$;
$C_3H_7$,
$C_4H_9$,or
$C_5H_{11}$; and n equals 1–20:
carboxyl$C_{1-20}$alkyl of the formula:

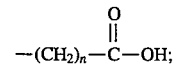

n=1–20;
$C_{1-20}$alkylcarbonyl$C_{1-20}$alkyl of the formula:

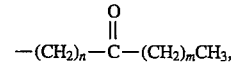

n equals 1–20;
m equals 0–19;
$C_{3-20}$cycloalkyl$C_{1-20}$alkyl of the formula:
—$(CH_2)n$-(cycloalkyl) wherein the cycloalkyl portion is a monocyclic, bicyclic, or polycyclic hydrocarbon of up to 20 carbon atoms wherein the rings are optionally substituted with $R^1$; and n=1–20;
aryl$C_{1-20}$alkyloxycarbonyl$C_{1-20}$alkyl of the formula:

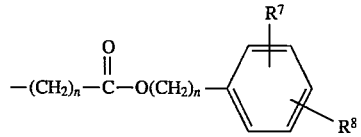

wherein $R^7$ and $R^8$ are as defined; n equals 1–20;
heteroaryl$C_{1-20}$alkyloxycarbonyl$C_{1-20}$alkyl of the formula:

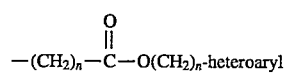

wherein heteroaryl is as defined and n=1–20;
halo$C_{1-20}$alkyl of the formula:

—$(CH_2)_n$—$CH_2X$ wherein

X equals Br, Cl, F or I; n is 1–19;
hydroxyl$C_{1-20}$alkyl of the formula:

—$(CH_2)_n CH_2OH$; n is 1–19;

halohydroxylC$_{1-20}$alkyl of the formula:

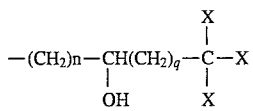

wherein
n=1–18
q=0–18
n+q=1–18 and
X equals Br, Cl, F or I;
arylC$_{1-20}$alkyloxyC$_{1-20}$alkyl of the formula:

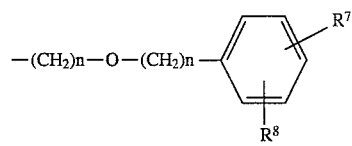

wherein
R$^7$ and R$^8$ are as defined; n is 1–20;
arylcarbonylaryC$_{1-20}$alkyl of the formula;

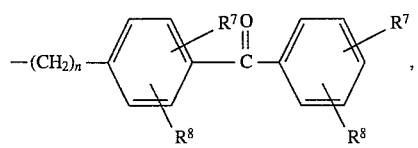

n equals 1–20;
diarylC$_{1-20}$alkyl of the formula:

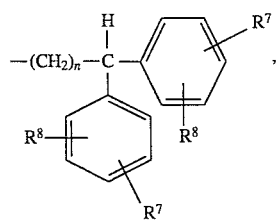

n equals 0–19;
triarylC$_{1-20}$alkyl of the formula:

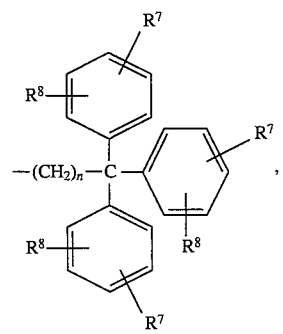

n equals 1–19;

aryl C$_{2-20}$alkenyl of the formula:

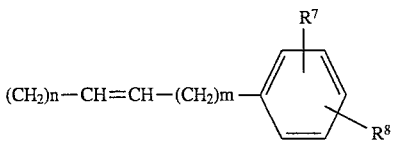

n=0–18
m=0–18
m+n=0–18
R$^4$ is:
H,
C$_{1-20}$ alkyl,
aryl, either unsubstituted or substituted with one of R, wherein R is H, C$_{1-6}$ alkyl, aryl C$_{1-20}$ alkyl with the alkyl groups unsubstituted or substituted with one of hydroxyl, C$_{1-8}$ alkyloxy, carboxy C$_{0-10}$ alkyl, or halogen or aryl directly substituted independently with one of amine, mono C$_{1-4}$ alkylamino, di C$_{1-4}$ alkylamino, mono C$_{1-4}$ alkylaminoaryl, di C$_{1-4}$ alkylaminoaryl, hydroxyl, halo C$_{1-20}$ alkyl, carboxamido, benzoyl, C$_{1-20}$ alkyloxy, C$_{1-20}$ alkyl, C$_{2-20}$ alkenyl, cyano, nitre, acetamide or halogen, or;
heteroaryl;
R$^5$ can be the same or different when x is greater than 1 and is:
H, or
C$_{1-12}$ alkyl;
R$^6$ is present when Z equals N and is independently
H,
C$_{1-20}$ alkyl, or
equivalent to R$^3$; or taken together with R$^3$ and the N to which they are attached represents a monocyclic mono N heteroaryl;
Y is:
O, or
S;
Z is:
N, or
O;
x is an integer from 1–10;
at each occurrence, aryl is phenyl;
at each occurrence, heteroaryl is independently selected from pyrrolyl, imidazolyl pyrazolyl, pyridyl, oxazolyl, isoxazolyl, thiazolyl, isothiazolyl, indolyl, quinolinyl, isoquinolinyl, benzimidazolyl, thiadiazolyl, benzopyranyl, benzothiazolyl, benzoxazolyl, furyl, thienyl, benzothienyl, and oxadiazolyl;
and dashes indicate a double bond is optionally present.

13. A pharmaceutical composition comprising a therapeutically effective amount of a compound of claim 1 and a pharmaceutically acceptable carrier.

14. The pharmaceutical formulation of claim 13, adapted for oral administration.

15. The pharmaceutical formulation of claim 13, adapted for topical administration.

16. A method of treating acne in a human host in need of such treatment, comprising the step of administering to the host a therapeutically effective amount of a compound defined in claim 1.

17. The method of claim 16 wherein the compound is administered orally.

18. The method of claim 16 wherein the compound is administered topically.

* * * * *

UNITED STATES PATENT AND TRADEMARK OFFICE
CERTIFICATE OF CORRECTION

PATENT NO. : 5,620,986

DATED : 4/15/97

INVENTOR(S) : BRUCE E. WITZEL ET AL.

It is certified that error appears in the above-indentified patent and that said Letters Patent is hereby corrected as shown below:

On the title of the page of the above U.S. Patent, the title of the invention should read: "17 UREA, THIOUREA, THIOCARBAMYL AND CARBAMYL 4-AZASTEROID 5ALPHA-REDUCTASE INHIBITORS USEFUL IN THE PREVENTION AND TREATMENT OF HYPERANDROGENIC DISORDERS".

At Column 40, in Claim 2, at line 66, insert "wherein".

At Column 44, in Claim 4, line 38 (the last line of the claim) should read "drostan-3-one, or 4-Methyl-20-(N'-thien-2-ylmethylureido)-5 α-4-azapregnan-3-one."

At Column 51, in Claim 12, line 13, delete "carboxamolic" and substitute therefor -- carboxamide --.

At Column 53, in Claim 12, line 13, delete "n+q=1-18" and substitute therefor -- n+q=0-18 --.

At Column 53, in Claim 12, line 25, delete "arylcarbonylary" and substitute therefor -- arylcarbonylaryl --.

At Column 54, in Claim 12, line 20, delete "amine" and substitute therfor -- amino --.

At Column 54, in Claim 12, line 24, delete "nitre" and substitute therefor -- nitro --.

At Column 54, in Claim 12, line 47, delete "imidazolyl pyrazolyl" and substitute therefor -- pyrazolyl, imidazolyl --.

Signed and Sealed this

Eighth Day of July, 1997

BRUCE LEHMAN

*Attest:*

*Attesting Officer*      *Commissioner of Patents and Trademarks*